US 9,526,430 B2

United States Patent
Srinivas et al.

(10) Patent No.: US 9,526,430 B2
(45) Date of Patent: Dec. 27, 2016

(54) METHOD AND SYSTEM TO ESTIMATE DAY-LONG CALORIE EXPENDITURE BASED ON POSTURE

(71) Applicant: Apple Inc., Cupertino, CA (US)

(72) Inventors: Umamahesh Srinivas, Santa Clara, CA (US); Hung A. Pham, Oakland, CA (US); Richard Channing Moore, III, San Francisco, CA (US); Alexander Singh Alvarado, Mountain View, CA (US); Xing Tan, San Jose, CA (US); Bharath Narasimha Rao, San Jose, CA (US); Mrinal Agarwal, Cupertino, CA (US); Karthik Jayaraman Raghuram, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 58 days.

(21) Appl. No.: 14/501,930

(22) Filed: Sep. 30, 2014

(65) Prior Publication Data
US 2016/0058329 A1     Mar. 3, 2016

Related U.S. Application Data

(60) Provisional application No. 62/044,846, filed on Sep. 2, 2014.

(51) Int. Cl.
*A61B 5/11*       (2006.01)
*A61B 5/0205*    (2006.01)
(Continued)

(52) U.S. Cl.
CPC .......... *A61B 5/0205* (2013.01); *A61B 5/0002* (2013.01); *A61B 5/0004* (2013.01);
(Continued)

(58) Field of Classification Search
CPC ............................ A61B 5/1116; A61B 5/1118
See application file for complete search history.

(56) References Cited

U.S. PATENT DOCUMENTS

| | | |
|---|---|---|
| 4,566,461 A | 1/1986 | Lubell et al. |
| 5,158,093 A | 10/1992 | Shvartz et al. |
| | (Continued) | |

OTHER PUBLICATIONS

Kunze, Kai, et al. "Where am i: Recognizing on-body positions of wearable sensors." Location-and context-awareness. Springer Berlin Heidelberg, 2005. 264-275.*

(Continued)

*Primary Examiner* — Michael C Stout
*Assistant Examiner* — Nicholas E Kolderman
(74) *Attorney, Agent, or Firm* — DLA Piper LLP (US)

(57) ABSTRACT

In one aspect, the present disclosure relates to a method, including obtaining, by the fitness tracking device, motion data of the user over a period of time, wherein the motion data can include a first plurality motion measurements from a first motion sensor of the fitness tracking device; determining, by the fitness tracking device, using the motion data an angle of the fitness tracking device relative to a plane during the period of time; estimating by the fitness tracking device, using the motion data, a range of linear motion of the fitness tracking device through space during the period of time; and comparing, by the fitness tracking device, the angle of the fitness tracking device to a threshold angle and comparing the range of linear motion of the fitness tracking device to a threshold range of linear motion to determine whether the user is sitting or standing.

20 Claims, 16 Drawing Sheets

(51) Int. Cl.
    A61B 5/00      (2006.01)
    A61B 5/024     (2006.01)
    A61B 5/22      (2006.01)
    A63B 22/06     (2006.01)
    G01C 22/00     (2006.01)
(52) U.S. Cl.
    CPC ...... *A61B 5/02416* (2013.01); *A61B 5/02438* (2013.01); *A61B 5/112* (2013.01); *A61B 5/1112* (2013.01); *A61B 5/1116* (2013.01); *A61B 5/1118* (2013.01); *A61B 5/1121* (2013.01); *A61B 5/1123* (2013.01); *A61B 5/222* (2013.01); *A61B 5/4866* (2013.01); *A61B 5/4884* (2013.01); *A61B 5/681* (2013.01); *A61B 5/6898* (2013.01); *A61B 5/725* (2013.01); *A61B 5/7221* (2013.01); *A61B 5/7246* (2013.01); *A61B 5/7264* (2013.01); *A61B 5/7275* (2013.01); *A63B 22/0605* (2013.01); *G01C 22/006* (2013.01); *A61B 2560/0204* (2013.01); *A61B 2560/0242* (2013.01); *A61B 2560/0475* (2013.01); *A61B 2562/0219* (2013.01)

(56) References Cited

U.S. PATENT DOCUMENTS

| | | | |
|---|---|---|---|
| 6,687,535 | B2 | 2/2004 | Hautala et al. |
| 7,771,320 | B2 | 8/2010 | Riley et al. |
| 7,841,967 | B1 | 11/2010 | Kahn et al. |
| 2009/0009320 | A1* | 1/2009 | O'Connor ............ A61B 5/1118 340/539.12 |
| 2010/0298656 | A1* | 11/2010 | McCombie ........ A61B 5/02028 600/301 |
| 2011/0040193 | A1 | 2/2011 | Seppanen et al. |
| 2011/0054359 | A1* | 3/2011 | Sazonov ............ A43B 3/0005 600/595 |
| 2011/0152695 | A1 | 6/2011 | Granqvist et al. |
| 2013/0023739 | A1 | 1/2013 | Russell |

OTHER PUBLICATIONS

Rowlands, Alex V., et al. "Assessing Sedentary Behavior with the GENEActiv: Introducing the Sedentary Sphere." Medicine and science in sports and exercise 46.6 (2014): 1235-1247.*

Gao, Lei, A. K. Bourke, and John Nelson. "Evaluation of accelerometer based multi-sensor versus single-sensor activity recognition systems." Medical engineering & physics 36.6 (2014): 779-785.*

Brooks, G.A. et al., "Exercise Physiology: Human Bioenergetics and Its Applications," Fourth Edition, McGraw Hill, ISBN 0-07-255642-0, Chapter 2: Bioenergetics, Chapter 10: Metabolic Response to Exercise: Lactate Metabolism During Exercise and Recovery, Excess Postexercise 02 Consumption (EPOC), O2 Deficit, O2 Debt, and the Anaerobic Threshold, Chapter 16: Cardiovascular Dynamics During Exercise, Chapter 21: Principles of Endurance Conditioning, Chapter 27: Exercise Testing and Prescription, 141 pages (2004).

Bruce, R.A. et al., "Exercising testing in adult normal subjects and cardiac patients," Pediatrics, vol. 32, No. Suppl., pp. 742-756 (Oct. 1963).

Bruce, R.A. et al., "Maximal oxygen intake and nomographic assessment of functional aerobic impairment in cardiovascular disease," American Heart Journal, vol. 85, Issue 4, pp. 546-562 (Apr. 1973).

Burke, Edmund R., "High-Tech Cycling," Second Edition, Human Kinetics, Chapter 4: Optimizing the Crank Cycle and Pedaling Cadence, Chapter 5: Cycling Biomechanics, Chapter 6: Cycling Power, Chapter 10: Physiology of Professional Road Cycling, Chapter 11: Physiology of Mountain Biking, 131 pages (2003).

Cavanagh, P.R. et al., "The effect of stride length variation on oxygen uptake during distance running," Medicine and Science in Sports and Exercise, vol. 14, No. 1, pp. 30-35 (1982).

Earnest, C.P. et al., "Cross-sectional association between maximal estimated cardiorespiratory fitness, cardiometabolic risk factors and metabolic syndrome for men and women in the Aerobics Center Longitudinal Study," Mayo Clin Proceedings, vol. 88, No. 3, pp. 259-270, 20 pages (Mar. 2013).

Fox, S.M. et al., "Physical Activity and the Prevention of Coronary Heart Disease," Bull. N.Y. Acad. Med., vol. 44, No. 8, pp. 950-967 (Aug. 1968).

Glass, S., et al., "ACSM's Metabolic Calculations Handbook," Lippincott Williams & Wilkins, 124 pages (2007).

Lavie, C.J. et al., "Impact of cardiorespiratory fitness on the obesity paradox in patients with heart failure," Mayo Clinic Proceedings, vol. 88, No. 3, pp. 251-258 (Mar. 2013).

Margaria, R. et al., "Energy cost of running," Journal of Applied Physiology, vol. 18, No. 2, pp. 367-370 (Mar. 1, 1963).

McArdle, W.D. et al., "Exercise Physiology: Nutrition, Energy and Human Performance," Seventh Edition, Lippincott Williams & Wilkins, Chapter 5: Introduction to Energy Transfer, Chapter 6: Energy Transfer in the Body, Chapter 7: Energy Transfer During Exercise, Chapter 8: Measurement of Human Energy Expenditure, Chapter 9: Human Energy Expenditure During Rest and Physical Activity, Chapter 10: Energy Expenditure During Walking, Jogging, Running and Swimming, Chapter 11: Individual Differences and Measurement of Energy Capacities, Chapter 21: Training for Anaerobic and Aerobic Power, 184 pages (2009).

Myers, J. et al., "Exercise Capacity and Mortality Among Men Referred for Exercise Testing," The New England Journal of Medicine, vol. 346, No. 11, pp. 793-801 (Mar. 14, 2002).

Noakes, Timothy D., "Lore of Running," Fourth Edition, Human Kinetics, Chapter 2: Oxygen Transport and Running Economy, Chapter 3: Energy Systems and Running Performance, 157 pages (2002).

Rapoport, Benjamin I., "Metabolic Factors Limiting Performance in Marathon Runners," PLoS Computational Biology, vol. 6, Issue 10, 13 pages (Oct. 2010).

Tanaka, H. et al., "Age-predicted maximal heart rate revisited," Journal of the American College of Cardiology, vol. 37, Issue 1, pp. 153-156 (Jan. 2001).

Wang, L. et al., "Time constant of heart rate recovery after low level exercise as a useful measure of cardiovascular fitness," Conf. Proc. IEEE Eng. Med. Biol. Soc., vol. 1, pp. 1799-1802 (2006).

* cited by examiner

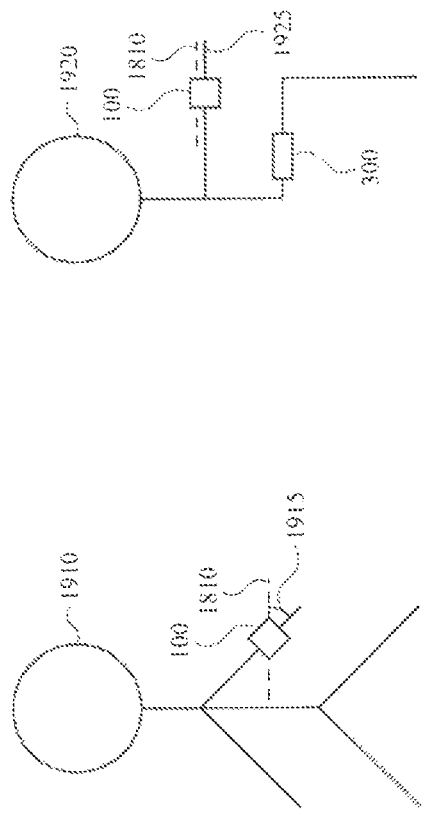
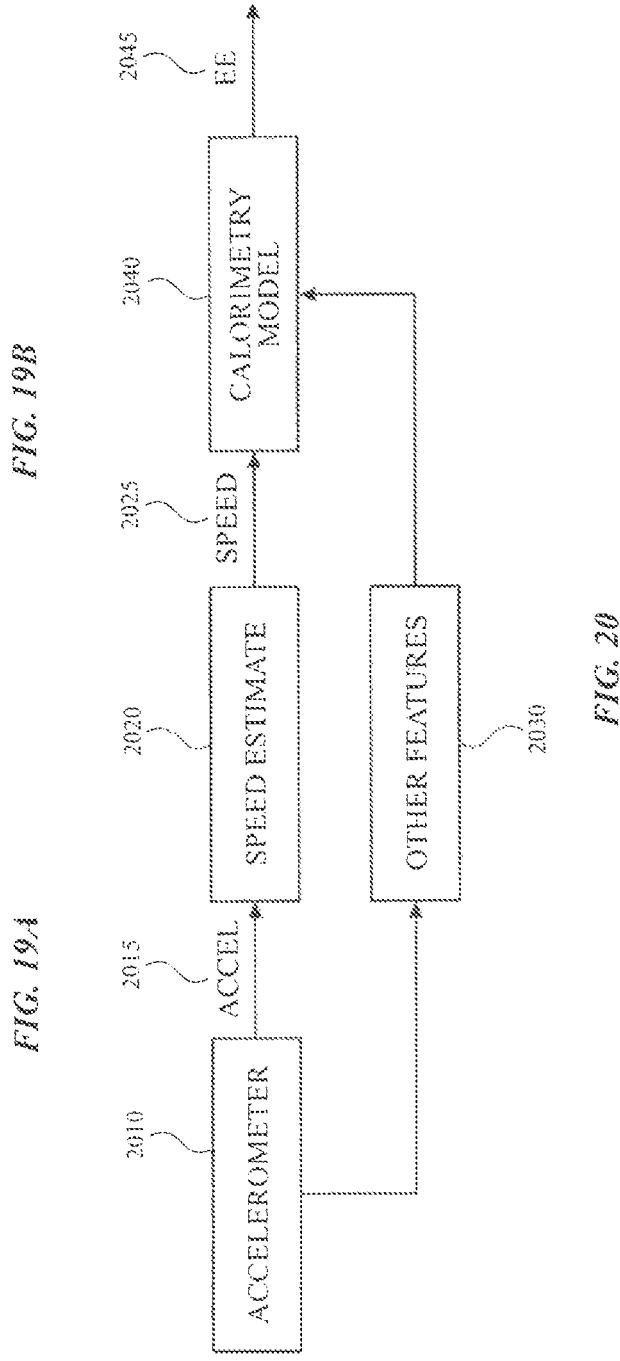
FIG. 19A
FIG. 19B
FIG. 20

METHOD AND SYSTEM TO ESTIMATE DAY-LONG CALORIE EXPENDITURE BASED ON POSTURE

PRIORITY

This application claims priority to U.S. Provisional Patent Application No. 62/044,846, titled "Calibration and Calorimetry Using Motion and Heart Rate Sensors," filed on Sep. 2, 2014, which is hereby incorporated by reference in its entirety.

CROSS-REFERENCE TO RELATED APPLICATIONS

This disclosure is related to U.S. Pat. application Ser. No. 14/501,634, titled "Method and System to Calibrate Fitness Level and Direct Calorie Burn Using Motion, Location Sensing. and Heart Rate," filed Sep. 30, 2014; U.S. patent application Ser. No. 14/501,771, titled "Accurate calorimetry for Intermittent Exercises," filed Sep. 30, 2014; U.S. patent application Ser. No. 14/502,754, titled "Sensor Fusion Approach to Energy Expenditure Estimation," filed Sep. 30, 2014; U.S. patent application Ser. No. 14/502,781, titled "Terrain Type Inference from Wearable with Motion Sensing," filed Sep. 30, 2014; U.S. patent application Ser. No. 14/502,809, titled "Method to Estimate Physical Activity Rating from Pedometer Data," filed Sep. 30, 2014; U.S. patent application Ser. No.14/502,701, titled "Local Model for Calorimetry," filed Sep. 30, 2014; U.S. Pat. application Ser. No. 14/502,827, titled "Latent Load Calibration for Calorimetry Using Sensor Fusion," filed Sep. 30, 2014; U.S. Provisional Patent Application No. 62/044,844, titled "Context-aware Heart Rate Estimation," filed Sep. 2, 2014; U.S. patent application Ser. No. 14/466,890, titled "Heart Rate Path Optimizer," filed on Aug. 22, 2014; and U.S. Provisional Patent Application No. 62/005,780, titled "Automatic Track Selection for Calibration of Pedometer Devices," filed on May 30, 2014; which are hereby incorporated by reference in their entirety.

FIELD

The present disclosure relates generally to improving calorie expenditure prediction and tracking and, more particularly, to techniques for calibration and calorimetry using data from motions sensors and heart rate sensors.

BACKGROUND

An individual's health or fitness can be assessed from the perspective of energy expenditure over time. One technique for estimating energy expenditure, or calorie burn, is based on heart rate. During moderate to vigorous exercise, heart rate relates linearly to energy expenditure.

At a macroscopic level, an individual's heart rate indicates how quickly the individual's body is delivering oxygen to vital organs and tissues, which consume the oxygen through oxidative cellular metabolism. The heart pumps blood through the lungs, where blood cells absorb oxygen from the lungs. This oxygen-rich blood returns to the heart, from which it is pumped through blood vessels that distribute the blood throughout the body to its organs and tissues. Tissues absorb oxygen carried by the blood and use the oxygen in chemical reactions of oxidative metabolism, also known as aerobic metabolism, to provide energy for biological functions.

The rate at which an individual body consumes oxygen at a given point in time is referred to as the volumetric flow of oxygen into the tissues of the body, also known as "oxygen uptake," or simply $\dot{V}O_2$ (e.g., liters of oxygen per minute). Controlling for differences in body size, $\dot{V}O_2$ is often reported for a given individual in terms of oxygen volume at standard temperature and pressure per unit of time per unit of body mass (e.g., ml/kg/min).

Specifically, $\dot{V}O_2$ measures the overall rate at which the body is engaged in oxidative metabolism. $\dot{V}O_2$ during various physical activities—and, consequently, energy expenditure during those physical activities—varies from individual to individual. In a laboratory setting, it may be possible to use indirect calorimetry (e.g., with a $\dot{V}O_2$ mask, heart rate monitors, etc.), to measure an individual's aerobic capacity, also known as maximum $\dot{V}O_2$, or simply "$\dot{V}O_2$max." $\dot{V}O_2$max is the maximum value of $\dot{V}O_2$ (e.g., measured with indirect calorimetry) that individual can consume.

Another measurement, related to $\dot{V}O_2$, is the Metabolic Equivalent of Task (MET), or simply "metabolic equivalent." Conventionally, 1 MET was defined to represent an "average" person's Resting Metabolic Rate (RMR) while sitting quietly. 1 MET was set to equal a $\dot{V}O_2$ of 3.5 ml/kg/min, or 1 kcal/kg/hr. Actual resting (or basal) metabolic rates will vary from one individual to the next. METs provide a way to compare calorie expenditure for different tasks. For example, if the task of walking slowly is designated as 2 METs (2 kcal/kg/hr), it signifies that walking slowly consumes twice as much energy as sitting quietly.

When these parameters are known, it may be possible to calibrate a fitness tracking device with more accurate calorimetry. Thus, at a given heart rate during moderate to vigorous aerobic exercise, a device may be capable of calculating a calorie burn rate that is calibrated for the individual. However, in practice, many individuals will not know their $\dot{V}O_2$max.

SUMMARY

Embodiments of the present disclosure include a fitness tracking device and techniques for accurately tracking an individual's energy expenditure over time and over a variety of activities while wearing the fitness tracking device. In some embodiments, the fitness tracking device may be a wearable device. The wearable device may be worn on a wrist, such as a watch, and it may include one or more microprocessors, a display, and a variety of sensors, including a heart rate sensor and one or more motion sensors.

Embodiments of the present disclosure may provide accurate, individualized calorimetry throughout a person's day, and across a variety of activities. Some embodiments may calibrate a fitness tracking device for an individual without necessarily relying on measuring $\dot{V}O_2$, heart rate testing, or self-reporting about physical activity. Additionally, some embodiments may model calorie burn and perform calorimetry processes for a variety of activities accurately, such as walking, running, cycling, or weight lifting. Also, some embodiments may use sensor data to estimate load (e.g., resistance, incline, grade, etc.) for exercise equipment such as elliptical trainers, step machines, treadmills, etc., and some embodiments may use sensor data to determine or predict a type of terrain (e.g., pavement, gravel, etc.), to model energy expenditure more accurately by taking these estimations into account. Furthermore, some embodiments may model calorie burn and perform calorimetry processes for sedentary and low-intensity activity (e.g., when not in an active exercise session), including sitting or standing.

In some embodiments, the heart rate sensor may include a photoplethysmogram (PPG) sensor for sensing heart rate. The PPG sensor can illuminate the user's skin using a light, such as a light-emitting diode (LED), and can measure changes in light absorption as blood is pumped through the subcutaneous tissue under the PPG sensor. The fitness tracking device can measure an individual's current heart rate from the PPG. The heart rate sensor may also be configured to determine a confidence level indicating a relative likelihood of an accuracy of a given heart rate measurement.

In some embodiments, the motion sensors may include, for example, an accelerometer, a gyroscope, etc. The fitness tracking device may also include a motion coprocessor, which may be optimized for low-power, continuous motion sensing and processing.

In some embodiments, the fitness tracking device may be capable of communicating with a companion device. The fitness tracking device may communicate with a companion device wirelessly, e.g., via a Bluetooth connection or similar wireless communication method. The companion device may be a second mobile device, such as a phone, which may include additional sensors. The additional sensors in the companion device may include a Global Positioning System (GPS) sensor, accelerometer, gyroscope, altimeter, motion coprocessor, etc. The companion device may, for example, communicate location information based on data from the GPS sensor to the fitness tracking device.

In some embodiments, a new fitness tracking device may be calibrated to measure energy expenditure based on heart rate and motion data. Out of the box, the new fitness tracking device may assume a default physical activity level ("PAL") for the user, which in turn may be used to estimate calorie burn for a variety of activities. As the user wears the new fitness tracking device over time, the new fitness tracking device may improve its estimate of the user's PAL. In some embodiments, the new fitness tracking device may consider a rolling average number of daily steps to adjust the user's PAL. Instead of, or in addition to, relying on pedometry to adjust the user's PAL, the new fitness tracking device may undergo active calibration by, for example, monitoring the user's heart rate and location information during at least a brief session of moderate to vigorous intensity (e.g., a ten-minute run).

In some embodiments, a fitness tracking device may apply particular models and algorithms based on prior calibration to compute energy expenditure given information about the user's heart rate, or motion, or a combination of the two. Energy expenditure computations may also take into account information from a companion device, such as GPS location information. The fitness tracking device may apply different models or different algorithms for different types of activity. For example, the fitness tracking device may use motion sensing information to determine whether a sedentary user is sitting down (burning relatively fewer calories) or standing up (burning relatively more calories).

In some embodiments, the fitness tracking device may apply yet another model for a user while walking, which may be based on pedometry and step counting.

In some embodiments, the fitness tracking device may improve the accuracy of its energy expenditure calculations by accounting for activity onset and cool down phases that occur, sometimes frequently, during intermittent physical activity such as weight lifting.

In some embodiments, the fitness tracking device may use a combination of motion and heart rate data to measure calorie burn during active and paced exercises such as running or cycling. Additionally, the fitness tracking device may make additional optimizations when a user is cycling by, for example, applying a work rate model that accounts for additional forces such as rolling resistance and aerodynamic drag. In some embodiments, the fitness tracking device may adjust the work rate model for cycling further by, for example, using motion data to detect the type of terrain on which the user is cycling.

In some embodiments, the fitness tracking device may use a combination of motion and heart rate data to estimate the load (or resistance) being, for example, generated by exercise equipment such as an elliptical trainer, step machine, etc.

In some embodiments, the fitness tracking device may use activity classification based on motion or heart rate data to automatically determine what type of physical activity (e.g., running) that a user is engaged in, and when that activity begins and ends. In other embodiments, the fitness tracking device may receive input from the user about when a user begins or ends an activity session, and what type of activity (e.g., running or cycling) the user is beginning or ending.

In some embodiments, the fitness tracking device may make further optimizations to compensate for limited system resources, such as limited battery power or limited memory capacity. For example, the fitness tracking device may decrease the frequency of instantaneous heart rate monitoring when a user is determined to be out of session, and increase the frequency of heart rate monitoring when a user is determined to be in session. For another example, the fitness tracking device may use local models to maintain highly accurate energy expenditure estimates while also significantly reducing the amount of power or memory needed to perform the calculations based on a local model technique as opposed to a nonlocal modeling technique. In some embodiments, the local models may be linear, quadratic, or higher order nonlinear equations.

In one aspect, the present disclosure relates to a method, including obtaining, by the fitness tracking device, motion data of the user over a period of time, wherein the motion data can include a first plurality motion measurements from a first motion sensor of the fitness tracking device; determining, by the fitness tracking device, using the motion data an angle of the fitness tracking device relative to a plane during the period of time; estimating by the fitness tracking device, using the motion data, a range of linear motion of the fitness tracking device through space during the period of time; and comparing, by the fitness tracking device, the angle of the fitness tracking device to a threshold angle and comparing the range of linear motion of the fitness tracking device to a threshold range of linear motion to determine whether the user is sitting or standing.

In some embodiments, the threshold angle is approximately 0 radians relative to the plane, wherein the plane is a horizontal plane, and wherein comparing the angle of the fitness tracking device to the threshold angle can include: determining, by the fitness tracking device, that the angle is less than the threshold angle; correlating, by the fitness tracking device, the angle of the fitness tracking device to an orientation of an arm of the user below the horizontal plane; and determining, by the fitness tracking device, that the user is standing.

In some embodiments, the threshold range of linear motion can be an interquartile range of linear motion of a first axis of an accelerometer of the fitness tracking device, and wherein comparing the range of linear motion of the fitness tracking device to the threshold range can include: determining, by the fitness tracking device, that the range of linear motion of the fitness tracking device is greater than the threshold range; correlating, by the fitness tracking device, the range of linear motion of the fitness tracking device to an amount of back-and-forth swaying of an arm of the user during the time period; and determining, by the fitness tracking device, that the user is standing.

In some embodiments, the method can include analyzing the motion data, by the fitness tracking device, to estimate a frequency of changing direction of linear motion of the fitness tracking device during the period of time; and comparing, by the fitness tracking device, the frequency of changing direction of linear motion to a threshold frequency of changing direction of linear motion to estimate whether the user is sitting or standing. In some embodiments, the method can include determining, by the fitness tracking device, that a companion device is inside a pocket of the user; receiving, by the fitness tracking device, orientation data of the companion device from a second motion sensor of a companion device via a wireless communication protocol; and analyzing, by the fitness tracking device, the orientation data of the companion device inside the pocket of the user to estimate whether the user is sitting or standing.

In some embodiments, the method can include determining, by the fitness tracking device, a first rate of energy expenditure of the user if the user is estimated by the fitness tracking device to be standing; and determining, by the fitness tracking device, a second rate of energy expenditure of the user if the user is estimated by the fitness tracking device to be sitting, wherein the first rate of energy expenditure for standing is higher than the second rate of energy expenditure for sitting. In some embodiments, the method can include resetting a sedentary timer of the fitness tracking device to zero seconds if the user is estimated by the fitness tracking device to be standing.

Another aspect of the present disclosure relates to fitness tracking device including a motion sensor for obtaining motion data of a user of the fitness tracking device; and a processor communicatively coupled to the motion sensor, wherein the processor is configured to: obtain motion data from the motion sensor over a period of time, wherein the motion data can include a first plurality motion measurements from the motion sensor of the fitness tracking device; determine, using the motion data, an angle of the fitness tracking device relative to a plane during the period of time; determine, using the motion data, a range of linear motion of the fitness tracking device through space during the period of time; and compare the angle of the fitness tracking device to a threshold angle and compare the range of linear motion of the fitness tracking device to a threshold range of linear motion to determine whether the user is sitting or standing.

In some embodiments, the threshold angle can be approximately 0 radians relative to the plane, wherein the plane is a horizontal plane, and wherein the processor is configured to: determine that the angle is less than the threshold angle; correlate the angle of the fitness tracking device to an orientation of an arm of the user below the horizontal plane; and determine that the user is standing. In some embodiments, the threshold range of linear motion can be an interquartile range of linear motion of a first axis of an accelerometer of the fitness tracking device, and wherein the processor is configured to: determine that the range of linear motion of the fitness tracking device is greater than the threshold range; correlate the range of linear motion of the fitness tracking device to an amount of back-and-forth swaying of an arm of the user during the time period; and determine that the user is standing. In some embodiments, the processor is configured to analyze the motion data to estimate a frequency of changing direction of linear motion of the fitness tracking device during the period of time; and compare the frequency of changing direction of linear motion to a threshold frequency of changing direction of linear motion to estimate whether the user is sitting or standing. In some embodiments, the processor is configured to determine that a companion device is inside a pocket of the user; receive orientation data of the companion device from a second motion sensor of a companion device via a wireless communication protocol; and analyze the orientation data of the companion device inside the pocket of the user to estimate whether the user is sitting or standing. In some embodiments, the processor is configured to determine a first rate of energy expenditure of the user if the user is estimated by the fitness tracking device to be standing; and determine a second rate of energy expenditure of the user if the user is estimated to be sitting, wherein the first rate of energy expenditure for standing is higher than the second rate of energy expenditure for sitting. In some embodiments, the device can include a sedentary timer, wherein the processor is configured to resent the sedentary timer to zero seconds if the user is estimated to be standing.

Another aspect of the present disclosure relates to an article of manufacture including a non-transitory processor readable storage medium; and instructions stored on the medium; wherein the instructions are configured to be readable from the medium by a processor of a fitness tracking device including a motion sensor for obtaining motion data of a user of the fitness tracking device and thereby cause the processor to operate so as to: obtain motion data from the motion sensor over a period of time, wherein the motion data includes a first plurality motion measurements from the motion sensor of the fitness tracking device; determine, using the motion data, an angle of the fitness tracking device relative to a plane during the period of time; determine, using the motion data, a range of linear motion of the fitness tracking device through space during the period of time; and compare the angle of the fitness tracking device to a threshold angle and compare the range of linear motion of the fitness tracking device to a threshold range of linear motion to determine whether the user is sitting or standing.

In some embodiments, the threshold angle can be approximately 0 radians relative to the plane, wherein the plane is a horizontal plane, and wherein the processor is caused to determine that the angle is less than the threshold angle; correlate the angle of the fitness tracking device to an orientation of an arm of the user below the horizontal plane; and determine that the user is standing. In some embodiments, the threshold range of linear motion can be an interquartile range of linear motion of a first axis of an accelerometer of the fitness tracking device, and wherein the processor is caused to determine that the range of linear motion of the fitness tracking device is greater than the threshold range; correlate the range of linear motion of the fitness tracking device to an amount of back-and-forth swaying of an arm of the user during the time period; and determine that the user is standing. In some embodiments, the processor is caused to analyze the motion data to estimate a frequency of changing direction of linear motion of the fitness tracking device during the period of time; and compare the frequency of changing direction of linear motion to a threshold frequency. In some embodiments, the processor is caused to: determine that a companion device is inside a pocket of the user; receive orientation data of the companion device from a second motion sensor of a companion device via a wireless communication protocol; and analyze the orientation data of the companion device inside the pocket of the user to estimate whether the user is sitting or standing. In some embodiments, the processor is caused to determine a first rate of energy expenditure of the user if the user is estimated by the fitness tracking device to be standing; and determine a second rate of energy expenditure of the user if the user is estimated to be sitting, wherein the first rate of energy expenditure for standing is higher than the second rate of energy expenditure for sitting.

Other features and advantages will become apparent from the following detailed description and drawings.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be illustrative only.

FIGS. 19A-B illustrate posture detection techniques in accordance with embodiments of the present disclosure.

FIG. 20 shows a speed-based calorimetry method in accordance with an embodiment of the present disclosure.

DESCRIPTION

There is growing interest to assess and monitor one's health or fitness and physical activity. The present disclosure describes a fitness tracking device that may be configured to provide an accurate, individualized quantification of energy expenditure over time and across a variety of activities. The device may implement sophisticated calorimetry techniques based on empirical models and sophisticated algorithms that may use motion data, heart rate data, or a weighted combination of both motion data and heart rate data.

Figure 1:
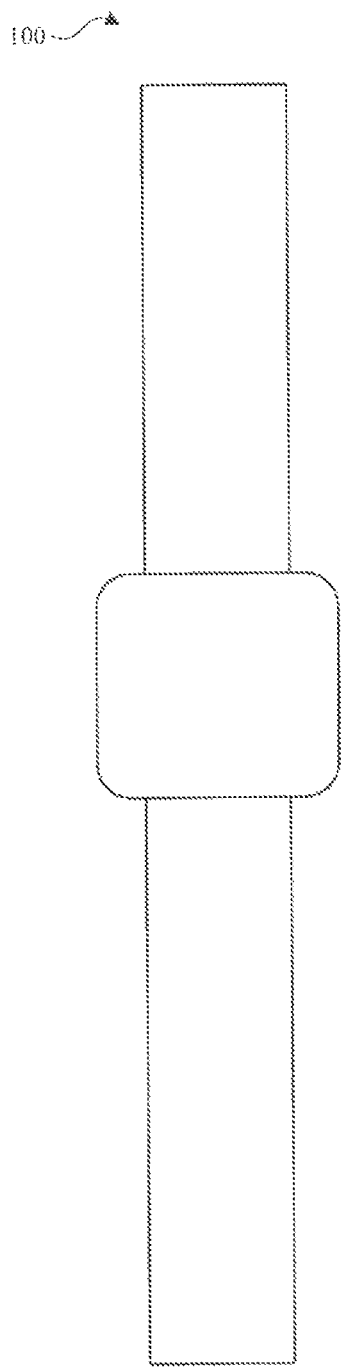
FIG. 1 shows a fitness tracking device in accordance with an embodiment of the present disclosure.

FIG. 1 shows an example of a fitness tracking device 100 in accordance with an embodiment of the present disclosure. In some embodiments, the fitness tracking device 100 may be a wearable device, such as a watch configured to be worn around an individual's wrist. As described in more detail below, the fitness tracking device 100 may be calibrated according to physical attributes of the individual and physical activity by the individual user who is wearing the fitness tracking device 100.

Figure 2:
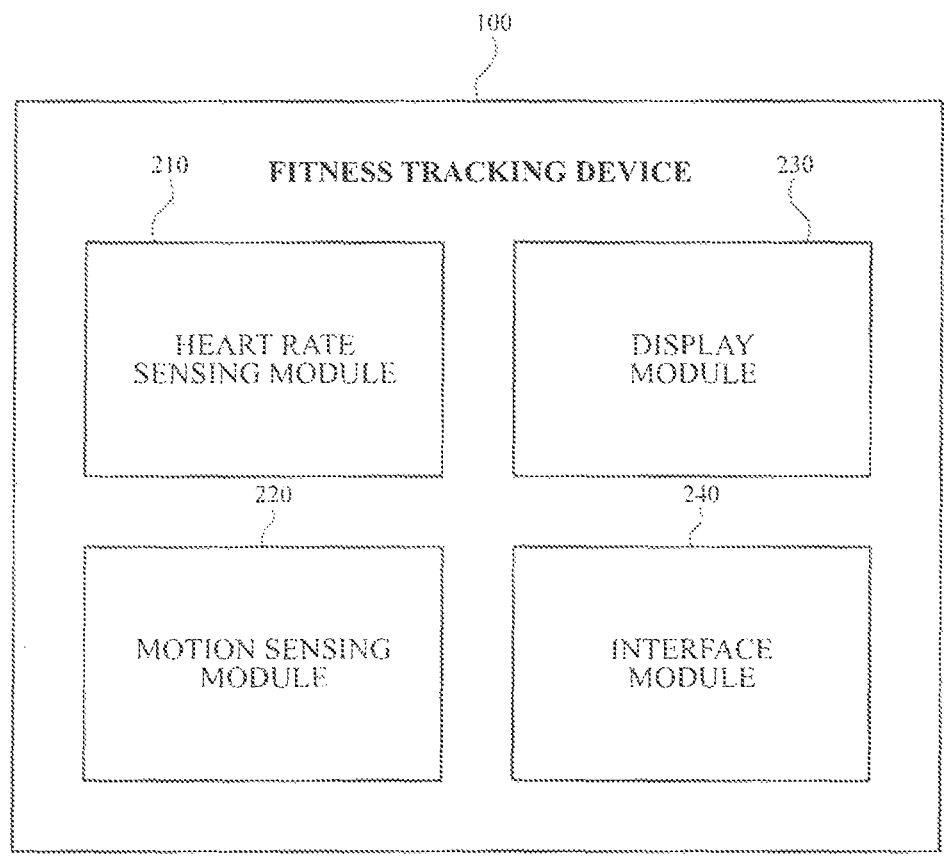
FIG. 2 depicts a block diagram of a fitness tracking device in accordance with an embodiment of the present disclosure.

FIG. 2 depicts a block diagram of example components that may be found within the fitness tracking device 100 in accordance with an embodiment of the present disclosure. These components may include a heart rate sensing module 210, a motion sensing module 220, a display module 230, and an interface module 240.

The heart rate sensing module 210 may include or may be in communication with a PPG sensor as previously described. The fitness tracking device can measure an individual's current heart rate from the PPG. The heart rate sensor may also be configured to determine a confidence level indicating a relative likelihood of an accuracy of a given heart rate measurement. In other embodiments, a traditional heart rate monitor may be used and may communicate with the fitness tracking device 100 through a near field communication method (e.g., Bluetooth).

The fitness tracking device 100 may include an LED and a photodiode or the equivalent to obtain a PPG. The fitness tracking device 100 may subsequently determine the user's current heart rate based on the PPG.

To conserve battery power on the fitness tracking device 100, the LED may be a relatively low-power LED, such as a green LED. In some embodiments, to further conserve power on the fitness tracking device 100, the fitness tracking device 100 may be configured to check heart rate at periodic intervals (e.g., once per minute, or once per three minutes). The period for checking heart rate may change dynamically. For example, if the fitness tracking device 100 automatically detects or receives input from the user that the user is engaged in a certain level, intensity, or type of physical activity (i.e., "in session"), the fitness tracking device may check heart rate more frequently (e.g., once per thirty seconds, once per minute, etc.). The fitness tracking device 100 may use, for example, machine learning techniques, battery power monitoring, or physical activity monitoring to balance the frequency of heart rate samples for accurate calorimetry with power optimization.

In addition to the heart rate sensing module 210, the fitness tracking device 100 may also include the motion sensing module 220. The motion sensing module 220 may include one or more motion sensors, such as an accelerometer or a gyroscope. In some embodiments, the accelerometer may be a three-axis, microelectromechanical system (MEMS) accelerometer, and the gyroscope may be a three-axis MEMS gyroscope. A microprocessor (not shown) or motion coprocessor (not shown) of the fitness tracking device 100 may receive motion sensing information from the motion sensors of the motion sensing module 220 to track acceleration, rotation, position, or orientation information of the fitness tracking device 100 in six degrees of freedom through three-dimensional space. As described in more detail herein, motion data obtained by the motion sensing module 220 may be used for a variety of purposes, including work rate modeling, automatic activity classification, pedometry, posture detection, cycling terrain identification, etc.

In some embodiments, the motion sensing module 220 may include other types of sensors in addition to accelerometers and gyroscopes. For example, the motion sensing module 220 may include an altimeter, or other types of location sensors, such as a GPS sensor.

In some embodiments, the fitness tracking device 100 may take advantage of the knowledge that the heart rate sensing module 210 and the motion sensing module 220 are approximately collocated in space and time to combine data from each module 210 and 220 to improve the accuracy of its calorimetry functionality. Depending on the current activity and a determination of a confidence of current heart rate and motion data, the fitness tracking device 100 may also rely on one of either the heart rate or a motion-derived work rate to estimate energy expenditure more accurately.

The fitness tracking device 100 may also include a display module 230. Display module 230 may be a screen, such as a sapphire or glass touchscreen, configured to provide output to the user as well as receive input form the user via touch. For example, display 230 may be configured to show the user a current heart rate or a daily average energy expenditure. Display module 230 may receive input form the user to select, for example, which information should be displayed, or whether the user is beginning a physical activity (i.e., starting a session) or ending a physical activity (i.e., ending a session), such as a running session or a cycling session. In some embodiments, the fitness tracking device 100 may present output to the user in other ways, such as by producing sound with a speaker (not shown), and the fitness tracking device 100 may receive input from the user in other ways, such as by receiving voice commands via a microphone (not shown).

In some embodiments, the fitness tracking device 100 may communicate with external devices via interface module 240, including a configuration to present output to a user or receive input from a user. Interface module 240 may be a wireless interface. The wireless interface may be a standard Bluetooth (IEEE 802.15) interface, such as Bluetooth v4.0, also known as "Bluetooth low energy." In other embodiments, the interface may operate according to a cellphone network protocol such as LTE or a Wi-Fi (IEEE 802.11) protocol. In other embodiments, interface module 240 may include wired interfaces, such as a headphone jack or bus connector (e.g., Lightning, Thunderbolt, USB, etc.).

The fitness tracking device 100 may be configured to communicate with a companion device 300 (FIG. 3), such as a smartphone, as described in more detail herein. In some embodiments, the fitness tracking device 100 may be configured to communicate with other external devices, such as a notebook or desktop computer, tablet, headphones, Bluetooth headset, etc.

The modules described above are examples, and embodiments of the fitness tracking device 100 may include other modules not shown. For example, the fitness tracking device 100 may include one or more microprocessors (not shown) for processing heart rate data, motion data, other information in the fitness tracking device 100, or executing instructions for firmware or apps stored in a non-transitory processor-readable medium such as a memory module (not shown). Additionally, some embodiments of the fitness tracking device 100 may include a rechargeable battery (e.g., a lithium-ion battery), a microphone or a microphone array, one or more cameras, one or more speakers, a watchband, a sapphire or glass-covered scratch-resistant display, water-resistant casing, etc.

Figure 3:
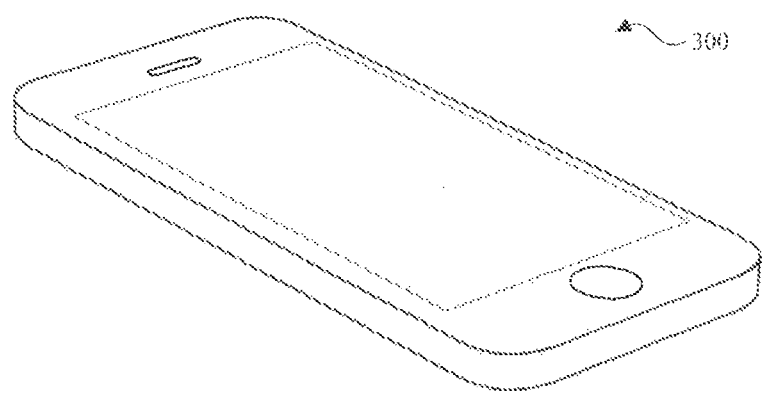
FIG. 3 shows a companion device in accordance with an embodiment of the present disclosure.

FIG. 3 shows an example of a companion device 300 in accordance with an embodiment of the present disclosure. The fitness tracking device 100 may be configured to communicate with the companion device 300, such as by a Bluetooth connection. In some embodiments, the companion device 300 may be a smartphone, tablet, or similar portable computing device. The companion device 300 may be carried by the user, stored in the user's pocket, strapped to the user's arm with an armband or similar device, placed on a table, or otherwise positioned within communicable range of the fitness tracking device 100.

The companion device 300 may include a variety of sensors, such as location and motion sensors (not shown). When the companion device 300 may be optionally available for communication with the fitness tracking device 100, the fitness tracking device 100 may receive additional data from the companion device 300 to improve or supplement its calibration or calorimetry processes. For example, in some embodiments, the fitness tracking device 100 may not include a GPS sensor as opposed to an alternative embodiment in which the fitness tracking device 100 may include a GPS sensor. In the case where the fitness tracking device 100 may not include a GPS sensor, a GPS sensor of the companion device 300 may collect GPS location information, and the fitness tracking device 100 may receive the GPS location information via interface module 240 (FIG. 2) from the companion device 300.

In another example, the fitness tracking device 100 may not include an altimeter, as opposed to an alternative embodiment in which the fitness tracking device 100 may include an altimeter. In the case where the fitness tracking device 100 may not include an altimeter, an altimeter of the companion device 300 may collect altitude or relative altitude information, and the fitness tracking device 100 may receive the altitude or relative altitude information via interface module 240 (FIG. 2) from the companion device 300.

Calibration—Overview

The following section describes calibration of the fitness tracking device 100 according to embodiments of the present disclosure. Three examples of methods of calibration described herein include: 1) default, or "out-of-the-box" calibration, 2) calibration by inferring a user's physical activity level, and 3) calibration based on "active," high-intensity heart rate and work rate data.

As explained above, an individual exhibits a linear relationship between heart rate (varying between the individual's minimum and maximum heart rates) and $\dot{V}O_2$ (up to the individual's aerobic capacity, or $\dot{V}O_2max$). Additionally, $\dot{V}O_2$ is linked to a user's aerobic power output based on the user's metabolic rate, which may also vary from one individual to the next. Metabolic rate may be expressed in Metabolic Equivalents of Task, or METs. METs indicates how many calories a "typical" individual burns per unit of body mass per unit of time.

If the user's weight is known, and the user undergoes testing to measure the user's maximum heart rate and $\dot{V}O_2$max, a device may be able to construct an individualized model of energy expenditure for a given heart rate.

In situations such as laboratory testing, it may be possible to test and measure a user's $\dot{V}O_2$max and maximum heart rate ("HRmax"). With these predetermined values, a device may be able to estimate energy expenditure more accurately based on a user's current heart rate during moderate to high-intensity physical activity or exercise. Without laboratory testing (e.g., testing based on indirect calorimetry), $\dot{V}O_2$max and HRmax may be estimated with other methods, such as submaximal exercise testing or non-exercise testing. For example, HRmax may be estimated based on the user's age. In some embodiments, if a heart rate greater than HRmax is observed, then the device may update the estimate of HRmax to use the higher, observed heart rate. In some embodiments, the device may determine whether to use an age-based estimate or a higher observed heart rate based on a confidence level for the heart rate measurement or whether the higher observed heart rate was sustained for a threshold period of time.

The user's minimum heart rate (HRmin or $HR_0$) and basal metabolic rate (e.g., $MR_0$) may be observed by the device as well or adjusted if even lower measurements are observed.

Calibration—Default Physical Activity Level (PAL)

Although a fitness tracking device 100 may be configured to calibrate itself based on heart rate measurements and other observations, when a user first takes a fitness tracking device 100 out of its box and wears it for the first time, the fitness tracking device 100 may not know the user's $\dot{V}O_2$max or other physical characteristics that it may need to measure energy expenditure more accurately.

Figure 4:
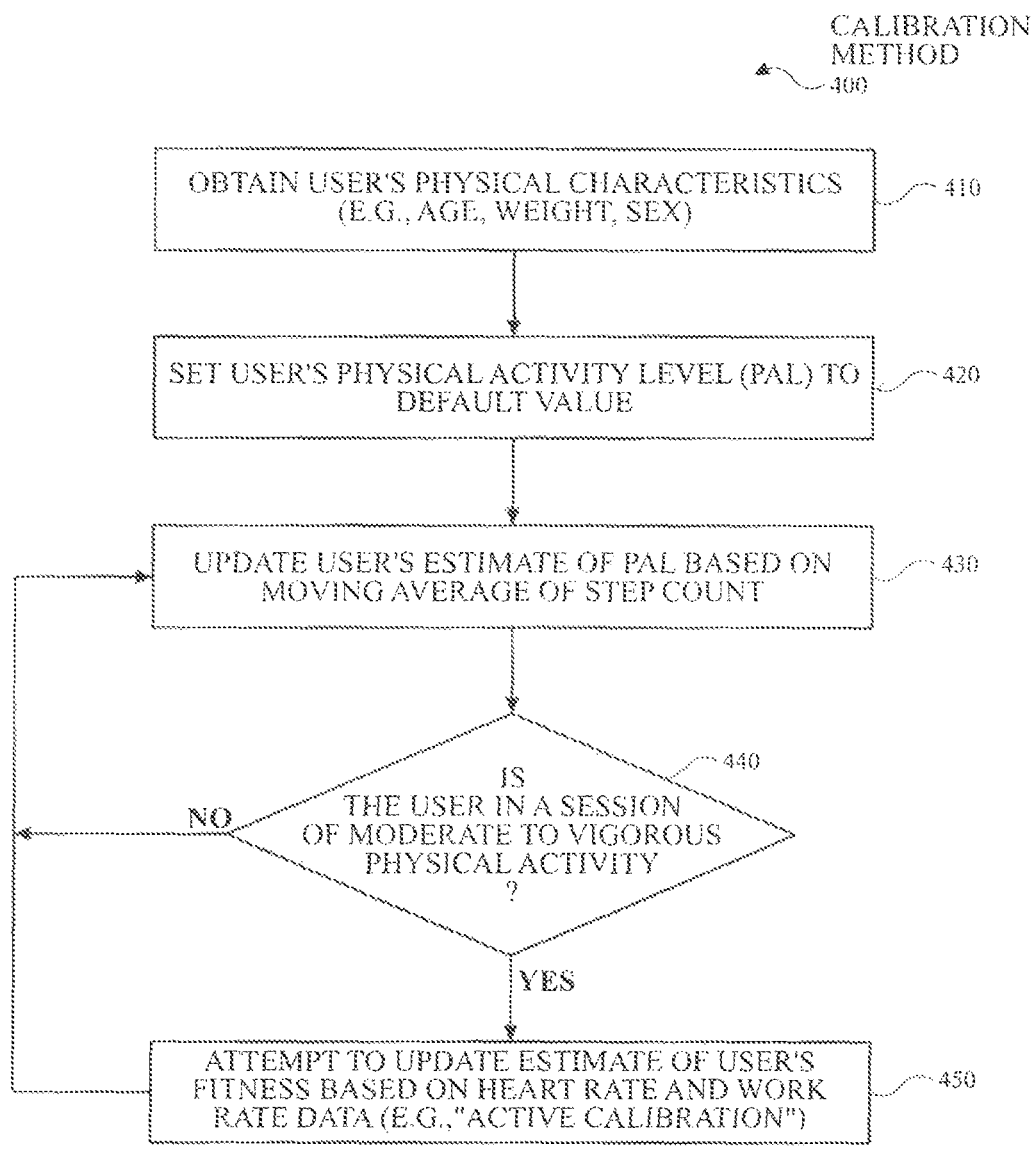
FIG. 4 shows a calibration method in accordance with an embodiment of the present disclosure.

FIG. 4 shows a calibration method 400 in accordance with an embodiment of the present disclosure. When a user wears, turns on, or otherwise uses a new fitness tracking device 100 for the first time, the fitness tracking device 100 may not have a record of any information about the physical characteristics or physical activity level ("PAL") of the user, or other information about the user such as heart rate data or work rate data.

At block 410, the user's physical characteristics may be obtained by the fitness tracking device 100. The obtained physical characteristics may include the user's age (e.g., based on the user's birth date, or based on a selected age, or based on a selected age range, etc.). The obtained physical characteristic's may also include the user's weight or weight range in, for example, pounds or kilograms. In some embodiments, the fitness tracking device 100 may automatically select or convert units according to the user's locale. The obtained physical characteristics may also include the user's sex (e.g., male or female).

In some embodiments, the fitness tracking device 100 may obtain this information automatically via interface module 240 (FIG. 2) from a companion device 300 (FIG. 3) or another device. In other embodiments, the fitness tracking device 100 may obtain this information from the user's account on a cloud-based data storage service after receiving the user's credentials to access the user's account. In other embodiments, the fitness tracking device 100 may obtain this information by prompting the user to provide it, such as via a touch-based interface or a voice-based interface.

The fitness tracking device 100 may be configured to store the user's physical characteristics in a memory module (e.g., a portion of a non-volatile NAND flash memory chip). In some embodiments, the fitness tracking device 100 may be configured to update a record of the user's physical characteristics at appropriate intervals. For example, the fitness tracking device 100 may be configured to increment the user's age annually on the user's birthday, or on the anniversary of the user's initial age selection, or at other suitable intervals. In some embodiments, the fitness tracking device 100 may periodically prompt the user to update the user's record of physical characteristics. For example, the fitness tracking device 100 may ask the user to input an updated weight once a week, or once a month, or other suitable intervals. In other embodiments, the fitness tracking device 100 may periodically poll the user's cloud-based data storage service account or poll the user's companion device 300 for updated information, or the fitness tracking device 100 may be configured to receive push notifications of updated physical characteristic information from the cloud-based data storage service, the companion device 300, or other devices.

At block 420, a default PAL may be set for the user. The PAL is a rating system, such as a 0-7 scale, or the 0-10 scale shown below in Table 1, or a scale that includes more than eleven levels. In the example of Table 1, a PAL score of 0 represents a lowest physical activity level (e.g., avoids walking or exercise), and a PAL score of 10 (or higher, in some embodiments) represents a highest physical activity level (e.g., over seven hours per week of heavy physical exercise). The PAL rating system may be based in part on the Physical Activity Rating (PA-R) rating system on a 0-7 scale. See Andrew S. Jackson et al., "Prediction of Functional Aerobic Capacity Without Exercise Testing," *Medicine and Science in Sports and Exercise*, Vol. 22.6 (1990), pp. 863-870, which is hereby incorporated by reference in its entirety. The PAL scores and descriptions in Table I are examples that may provide a parameter to an energy expenditure model for calorimetry, such as a model based at least in part on the research by Jackson et al. In other embodiments, other ranges of physical activity levels may be used, or other techniques for applying PAL scores in an energy expenditure model may be used.

TABLE I

Physical Activity Level ("PAL") Scoring Sheet

| PAL Score | Description of Corresponding Level of Activity |
|---|---|
| 0-1 point: | Does not participate regularly in programmed recreation, sport, or physical activity: |
| 0 points | Avoids walking or exercise (e.g., always uses elevators, drives whenever possible instead of walking) |
| 1 point | Walks for pleasure, routinely uses stairs, occasionally exercises sufficiently to cause heavy breathing or perspiration |
| 2-3 points: | Participates regularly in recreation or work requiring modest physical activity (such as golf, horseback riding, calisthenics, gymnastics, table tennis, bowling, weight lifting, or yard work): |
| 2 points | 10-60 minutes per week of aforementioned activities |
| 3 points | Over 1 hour per week of aforementioned activities |
| 4-7 points: | Participates regularly in heavy physical exercise (such as running or jogging, swimming, cycling, rowing, skipping rope, or running in place), or engages in vigorous aerobic-type activities (such as tennis, basketball, or handball): |
| 4 points | Runs less than 1 mile per week or spends less than 30 minutes per week in comparable physical activity |
| 5 points | Runs 1-5 miles per week or spends 30-60 minutes per week in comparable physical activity |
| 6 points | Runs 5-10 miles per week or spends 1-3 hours per week in comparable physical activity |

TABLE I-continued

Physical Activity Level ("PAL") Scoring Sheet

| PAL Score | Description of Corresponding Level of Activity |
|---|---|
| 7 points | Runs more than 10 miles per week or a comparable physical activity |
| 8-10 points: Participates in heavy physical exercise for a significant amount of time per week: | |
| 8 points | 3-5 hours per week of "heavy physical exercise" |
| 9 points | 5-7 hours per week of "heavy physical exercise" |
| 10 points | Over 7 hours per week of "heavy physical exercise" |

As shown in Table I, some levels may be inferred based on distance (if distance information is available), or they may be inferred based on time. The parameters and descriptions for each level in Table I are merely examples, and any suitable number of levels or suitable distinguishing features of each level may be used. For example, PAL level 5 could be adjusted to require running more miles (e.g., 2-5 miles) or spending more time per week in comparable physical activity (e.g., 45-60 minutes).

The default PAL score may be set to, for example, 2 points, or 3 points. In some embodiments, a first default PAL score (e.g., 2) may be selected for a first user in a first locale, and a second default PAL score (e.g., 3) may be selected for a second user in a second locale. In other embodiments, a default PAL score (e.g., 2 or 3) may be selected based at least in part on a predetermined "typical" PAL score for a group of users with similar physical characteristics as the physical characteristics obtained for the user at block 410.

The fitness tracking device 100 may be configured to select a default PAL score so as to avoid requiring or otherwise requesting the user to self-report a PAL score. For example, a nutritionist or physical trainer might provide a client with a survey to help assess the client's PAL score. Moreover, self-reported PAL scores may not necessarily be accurate because the client may not necessarily be able to answer the survey questions accurately. By selecting a default PAL score, it may not be necessary for the fitness tracking device 100 to present a new user with a similar survey, which may decrease setup time for a new fitness tracking device 100 and improve the user's overall setup or onboarding user experience.

For a typical or average user, a default PAL score such as 2 may be accurate, if the user engages in 10-60 minutes of modest physical activity. For other users, it is possible that a default PAL score such as 2 may either overestimate or underestimate the actual physical activity level of the user. For example, the default score may be an underestimate for an ultra-marathoner, who may have an actual physical activity level equivalent to a PAL score of 10 (or higher, in some embodiments). Similarly, the default PAL score may be an overestimate for a user who does not exercise and avoids walking. In turn, the calorimetry process may overestimate or underestimate the user's energy expenditure throughout the day based on a model, such as the Jackson et al. model, when using an inaccurate PAL score. However, as explained in detail below, after the user begins wearing the fitness tracking device 100, the fitness tracking device 100 may be configured to recalibrate the calorimetry model within a short period of time by, e.g., inferring updated PAL scores, regardless of whether the user engages in exercise or what type of physical activity the user performs.

At block 440, the fitness tracking device 100 may determine whether the user is engaged in a session of moderate to vigorous physical activity. If the user is determined not to be engaged in a session of moderate to vigorous physical activity (e.g., the user is engaged in modest or otherwise low-intensity physical activity, or the user is sedentary), calibration method 400 may return to block 430. If the user is determined to be engaged in a session of moderate to vigorous physical activity (e.g., running), calibration method 400 may proceed to block 450.

It may be understood that, in some embodiments, a substantial amount of time may pass during calibration method 400. For example, a first user may go for a run (i.e., proceeding to block 450) within minutes of turning on the fitness tracking device 100 for the first time, whereas a second user may not go for a run for several months (if ever) after turning on the fitness tracking device 100 for the first time. In the interim, the fitness tracking device 100 may continuously or otherwise periodically update each user's individualized PAL score based at block 430 as described below.

After performing recalibration at either block 430 or block 450, calibration method 400 may return to block 440 to reassess whether the user is engaged in moderate to vigorous physical activity. Thus, the fitness tracking device 100 may continue to recalibrate or otherwise adjust one or more energy expenditure models for calorimetry as the fitness tracking device 100 collects more data about a user's fitness and activity levels or as the user's fitness or activity levels change over time.

Calibration—Physical Activity Level Score Recalibration

As previously explained, an energy expenditure model may take into account a physical activity level (PAL) score of a user to perform calorimetry processes more accurately. The fitness tracking device 100 may collect data on the user's activity, such as an output from a pedometer function or other activity classifier, to update the PAL score for a user.

Figure 5:
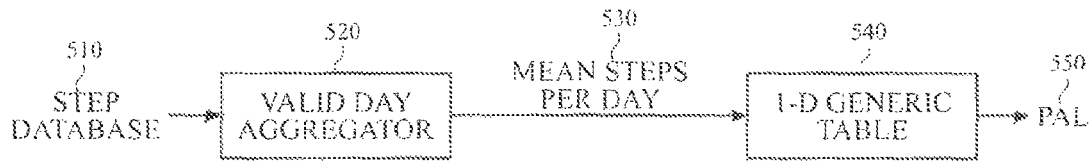
FIG. 5 depicts a block diagram of a calibration technique for inferring physical activity level in accordance with an embodiment of the present disclosure.

FIG. 5 depicts a block diagram of a calibration technique for inferring Physical activity level in accordance with an embodiment of the present disclosure. As shown in FIG. 5, the fitness tracking device 100 may access a step database 510. The step database 510 may be stored in a memory module of the fitness tracking device 100, or the step database 510 may be accessible from another device or a cloud-based storage service via interface module 240 (FIG. 2) of the fitness tracking device 100.

The step database 510 maintains records of data about a user's activity. In a particular example, the step database may store records based on an estimated number of steps that the user has taken for each day over a sequence of days based on the output of a pedometer of the fitness tracking device 100. In some embodiments, the pedometer of the fitness tracking device 100 may be implemented using data from one or more motion sensors in motion sensing module 220 (FIG. 2).

In some embodiments, a valid day aggregator 520 will receive activity information such as daily step count information from the step database 510. The valid day aggregator 520 may determine a moving average for mean steps per day 530 based on a rolling window (e.g., a seven-day rolling window) of data from the step database 510. In some embodiments, if a smaller rolling window of time is preferred, or if fewer than seven days are available during the first week of use, a smaller rolling window may be used, such as 3 days, or 5 days.

In some embodiments, the valid day aggregator 520 will disregard records from the step database 510 that the valid day aggregator 520 may determine to be "invalid days." For example, if the user forgets to wear the fitness tracking device 100 for most of the day, or if the fitness tracking device 100 is turned off or a battery of the fitness tracking device 100 is drained during most of a day, the total step count for that day may be artificially low. The valid day aggregator 520 may discard a total step count for a day if the total step count is less than a threshold number of steps (e.g., fewer than 500 steps, or fewer than 1,000 steps).

Thus, if the size of the rolling window is seven days, but the user forgot to wear the fitness tracking device 100 for one of the most recent seven days, the valid day aggregator 520 may discard that day from its computation and, instead, use the total step count from the eighth most recent day to provide a total of seven "valid days" to be aggregated. The valid day aggregator 520 may output a mean steps per day 530 that was computed using only valid days because the valid day aggregator 520 may have filtered out the invalid days within the rolling window of time.

The fitness tracking device 100 may use the mean steps per day 530 determined by the valid day aggregator 520 to lookup a corresponding PAL score 550 from a table, such as a one-dimensional user-specific table 540, described in more detail herein with reference to Table II below:

TABLE II

One-Dimensional Look-up Table

| Minimum Mean Steps per Day | Corresponding Estimated PAL Score |
|---|---|
| 0 | 0 points |
| 1,000 | 1 point |
| 2,000 | 2 points |
| 3,800 | 3 points |
| 5,000 | 4 points |
| 6,500 | 5 points |
| 9,000 | 6 points |
| 11,000 | 7 points |
| 14,000 | 8 points |
| 17,000 | 9 points |
| 20,000 | 10 points |

Table II shows a one-dimensional table (e.g., the one-dimensional user-specific table 540) in accordance with an embodiment of the present disclosure. The one-dimensional user-specific table 540 correlates a minimum (or range of) mean steps per day to a particular PAL score. In the example one-dimensional user-specific table 540 shown in FIG. 6, each PAL score 0 to 10 has a corresponding minimum number of steps. For example, a user would need to have at least 5,000 mean steps per day for the fitness tracking device 100 to estimate that the user has a PAL score of 4 if using Table II. Similarly, if the mean steps per day 530 is greater than or equal to 20,000 steps, the user's PAL score will be updated to 10, according to the one-dimensional user-specific table 540 shown in Table II. The range of PAL scores, as well as the default range of steps correlated to each PAL score, may vary in other embodiments.

In some embodiments, each range of steps is estimated based on the activity level associated with each PAL score. The total number of steps $S_{total}$ for the low end and high end of each range is a sum of the steps attributable to base-level activity (i.e., daily living activity) $S_{base}$, steps attributable to modest activity $S_{mod}$, and steps attributable to heavy exercise $S_{heavy}$:

$$S_{total}=S_{base}+S_{mod}+S_{heavy} \quad \text{(Eq. 1A)}$$

The fitness tracking device 100 may assume, at least initially, that base activity and modest activity correlates to a typical walking cadence $C_w$ (e.g., 100 steps/min, or 120 steps/min) or a typical walking step length or stride length $L_w$ (e.g., 0.6 m/step, or 0.8 m/step), and that heavy activity correlates to a typical running cadence $C_r$ (e.g., 150 steps/min) and a typical running step length or stride length $L_r$ (e.g., 1 m/step). These default or typical values may be scaled or otherwise adjusted up or down according to an individual user's typical cadence while walking or running and stride length while running. For example, the fitness tracking device 100 may be configured to provide a more accurate individualized stride length based on the user's height. In some embodiments, the fitness tracking device 100 may be configured to request the user's height from the user or otherwise obtain the user's height from, for example, the companion device 300.

Thus, total steps $S_{mod}$ during base activity or modest activity may be computed as a product the time t spent engaged in base activity or modest activity with a typical cadence $C_w$ (for the portion of base activity or modest activity measured based on time) plus the number of steps based on walking stride length (for the portion of base activity or modest activity measured based on distance d traversed):

$$S_{base}=t \cdot C_w + d/L_w \quad \text{(Eq. 1B)}$$

$$S_{mod}=t \cdot C_w + d/L_w \quad \text{(Eq. 1C)}$$

Additionally, total steps $S_{heavy}$ during heavy activity may be computed with a typical running cadence $C_r$ (for the portion of heavy activity measured based on time t spent performing the heavy activity) and/or a typical running stride length $L_r$ (for the portion of heavy activity measured based on distance d traversed):

$$S_{heavy}=t \cdot C_r + d/L_r \quad \text{(Eq. 1D)}$$

For example, PAL score 3 corresponds to at least 60 minutes (i.e., a time-based parameter) of modest physical activity (i.e., an activity-based parameter). The fitness tracking device 100 may assume, at least initially, that modest physical activity correlates to a typical walking cadence (e.g., 100 steps/min).

Thus, in this example, the amount of base activity for PAL score 3 may be assumed to be a certain amount of time (e.g., approximately 30 min/day of base activity, or in other embodiments, e.g., 45 minutes/day of base activity). Thus, in this example, a minimum means steps/day may account for steps attributable to base activity, which may be computed by multiplying the time of 30 min/day by the default cadence of 100 steps/min, which equals 3,000 steps/day.

Similarly, in this example, the minimum mean steps per day for PAL score 3 may include steps attributable to modest activity, which may be computed by multiplying by the low-end time of 60 minutes/week by the default cadence of 100 steps/min, which equals 6,000 mean steps/week (or approximately 800 steps/day).

In this example, PAL score 3 is assumed to include no amount of heavy exercise, so $S_{heavy}$ equals 0, and $S_{total}$ equals approximately 3,800 steps/day. This value is reflected as the low end total number of steps needed for a user to qualify for a PAL score of 3 according to Table II.

In another example, PAL score 5 may be assumed to include at least: 1) 60 min/day of base activity at 100 steps/min, or 6,000 steps/day, plus 2) 30 min/week of modest exercise at 100 steps/min, or approximately 400 steps/day, plus 3) 1 mile/week of heavy exercise, or approximately 100 steps/day, for a total of at least 6,500 (mean) steps/day. This value corresponds to the minimum means steps per day correlated to PAL score 5 using Table II.

Similar step-based estimations and computations may be similarly made to generate the low and high ends of each step range for each PAL score. The parameters (e.g., cadences and stride lengths) may be calibrated or otherwise adjusted to the individual user, and these parameters may be used for both generating the one-dimensional user-specific table 540 as well as for computing the user's steps throughout the day (e.g., by a pedometer, or other activity-tracking functions, based on the motion sensing module 220 of the fitness tracking device 100).

Figure 6:
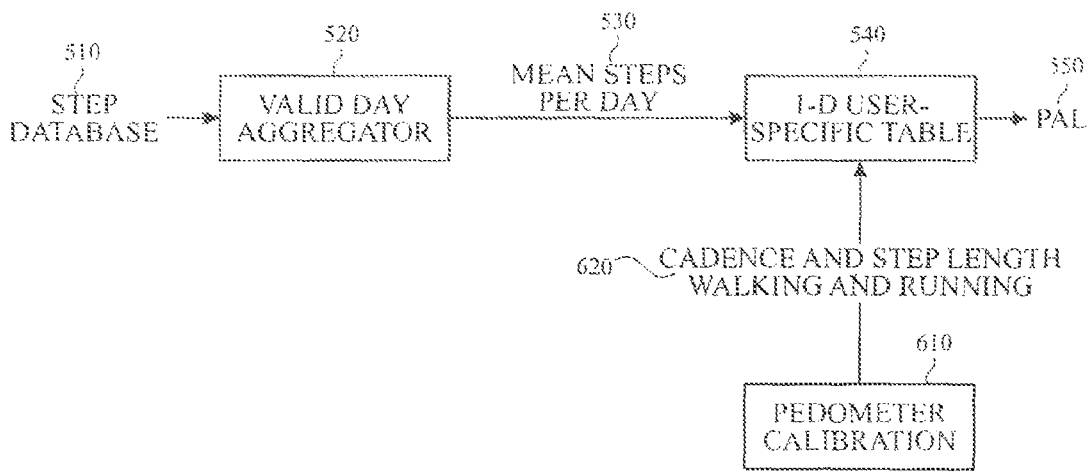
FIG. 6 depicts a block diagram of a calibration technique for inferring physical activity level in accordance with an embodiment of the present disclosure.
Figure 7:
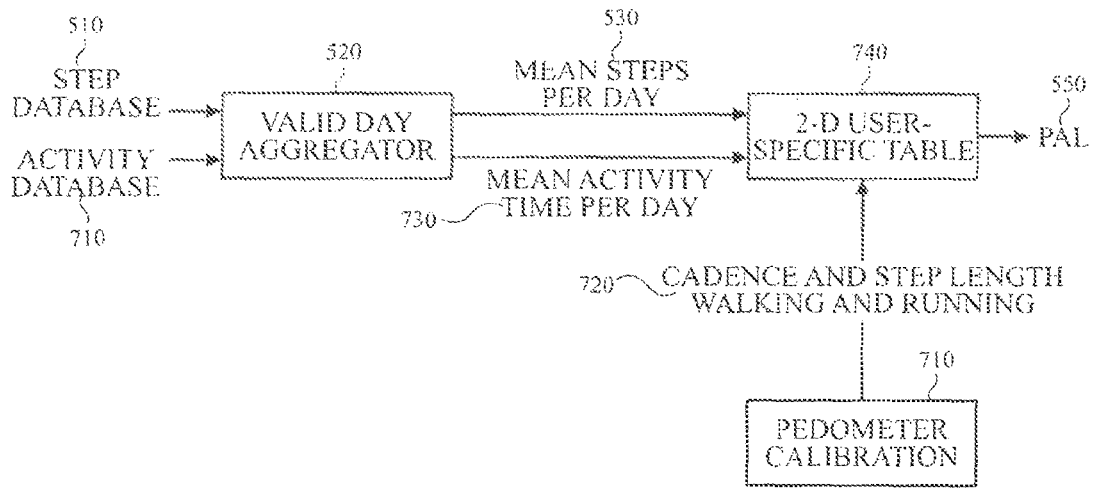
FIG. 7 depicts a block diagram of a calibration technique for inferring physical activity level in accordance with an embodiment of the present disclosure.

FIG. 7 depicts another block diagram of a calibration technique for inferring physical Activity level in accordance with an embodiment of the present disclosure. In FIG. 6, pedometer calibration module 610 may calibrate the pedometer functionality of the fitness tracking device 100. Additionally, pedometer calibration module 610 may output individualized or otherwise calibrated cadence and step length values for walking and running (620), which may be used to generate the one-dimensional user-specific table 540 (e.g., Table II above).

Pedometer calibration may account for differences among users. For example, consider one runner who has a relatively high running cadence when compared to a second runner who has a relatively low running cadence. If both runners run for one hour, the first runner with the higher cadence will take more steps than the second runner with the lower cadence. Consequently, in some embodiments, the first runner with the higher cadence may be expected to take more steps to qualify for a given PAL score than the second runner.

In some embodiments, the fitness tracking device 100 may determine a user's PAL score based on a total number of steps that does not differentiate between which steps originated from base, modest, or heavy activity, or whether the activity was measured based on time or distance. In this case, the fitness tracking device 100 will consider the aggregated number of steps as a single dimension of information for correlating activity to a PAL score.

In other embodiments, additional accuracy may be achieved by differentiating among the different activity sources to more closely correlate with the descriptions of each PAL score, which also differentiate among different types of activity. The aggregated number of steps may not indicate the sources of the steps, such as how many steps can be attributed to running as opposed to lower intensity activities such as walking Consequently, two users with the same aggregated step count but who engage in different physical activities may have different physical activity levels. As explained below, the fitness tracking device 100 may be configured to select or adjust a user's PAL level by considering information about the user's activities in addition to the user's aggregated step count.

FIG. 7 depicts another block diagram of a low-intensity calibration technique in accordance with an embodiment of the present disclosure. As shown in FIG. 7, an activity database 710 provides additional records of user data to the valid day aggregator 520. The activity database 710 may be a part of the steps database 510, or it may be a separate database. The activity database may include a table with a row for each day. Each row in the table, or database record, may track various information, including, but not limited to, time spent or steps taken in base (or "background") activities; time spent, distance traversed, or steps taken in modest activity; and time spent, distance traversed, or steps taken in heavy activity. In some embodiments, the pedometer functionality or another activity classifier module may be configured to distinguish among base activity, modest activity, and heavy activity. In other embodiments, the fitness tracking device 100 may be configured to accept user input to determine when a user is going to be "in-session" for a particular activity, such as going for a run or a bike ride, and the fitness tracking device 100 may record this information accordingly in the activity database 710.

In some embodiments, the valid day aggregator 520 may use information from both the steps database 510 and the activity database 710 to provide two (or more) dimensions of data to look up PAL scores in a user-specific table of two-dimensions (or more). FIG. 7 depicts the valid day aggregator 520 outputting both the mean steps per day 530 as well as a mean activity time per day 730, both of which may be determined based on a rolling average as described above with reference to FIG. 5.

Both the mean steps per day 530 and the mean activity time per day 730 may be used as input to a two-dimensional user-specific table 740 (e.g., Table III below). The two-dimensional user-specific table 740 may also be calibrated according to the pedometer calibration module 610 and the individualized cadence and step length values 620 to customize the two-dimensional user-specific table 740 to a specific user, similarly as explained above with reference to FIG. 6. The look-up function into the two-dimensional user-specific table 740 (e.g., Table III below) may be configured to output the PAL score that correlates to both dimensions of input data:

TABLE III

Two-Dimensional Look-up Table

| Low Activity | | High Activity | |
|---|---|---|---|
| Minimum Mean Steps per Day | Corresponding Estimated PAL Score (Low Activity) | Minimum Mean Steps per Day | Corresponding Estimated PAL Score (High Activity) |
| 0 | 0 points | 0 | 0 points |
| 1,000 | 1 point | 500 | 2 points |
| 2,000 | 2 points | 1,500 | 3 points |
| 3,800 | 3 points | 2,500 | 4 points |
| 5,000 | 4 points | 4,000 | 5 points |
| 6,500 | 5 points | 5,500 | 6 points |
| 9,000 | 6 points | 9,000 | 6 points |
| 11,000 | 7 points | 11,000 | 7 points |
| 14,000 | 8 points | 14,000 | 8 points |
| 17,000 | 9 points | 17,000 | 9 points |
| 20,000 | 10 points | 20,000 | 10 points |

Table III (above) shows an example of a two-dimensional user-specific table 740 in accordance with an embodiment of the present disclosure. Like the one-dimensional user-specific table 540 described with reference to Table II, the two-dimensional user-specific table 740 also correlates a range of mean steps per day (i.e., step ranges 900-911) with a PAL score of 0-11. However, in this example of the two-dimensional user-specific table 740, some step ranges overlap with other step ranges. For example, step range 900, which correlates to PAL score 0, ranges from 2,180 to 4,300 steps, while step range 901, which correlates to PAL score 1, ranges from 3,500 to 4,500 steps. Thus, mean steps per day 530 may be insufficient to determine a unique step range and output a unique PAL score. For example, if mean steps per day 530 equals 4,000 steps, that value by itself may indicate either PAL score 0 or PAL score 1.

Figure 9:
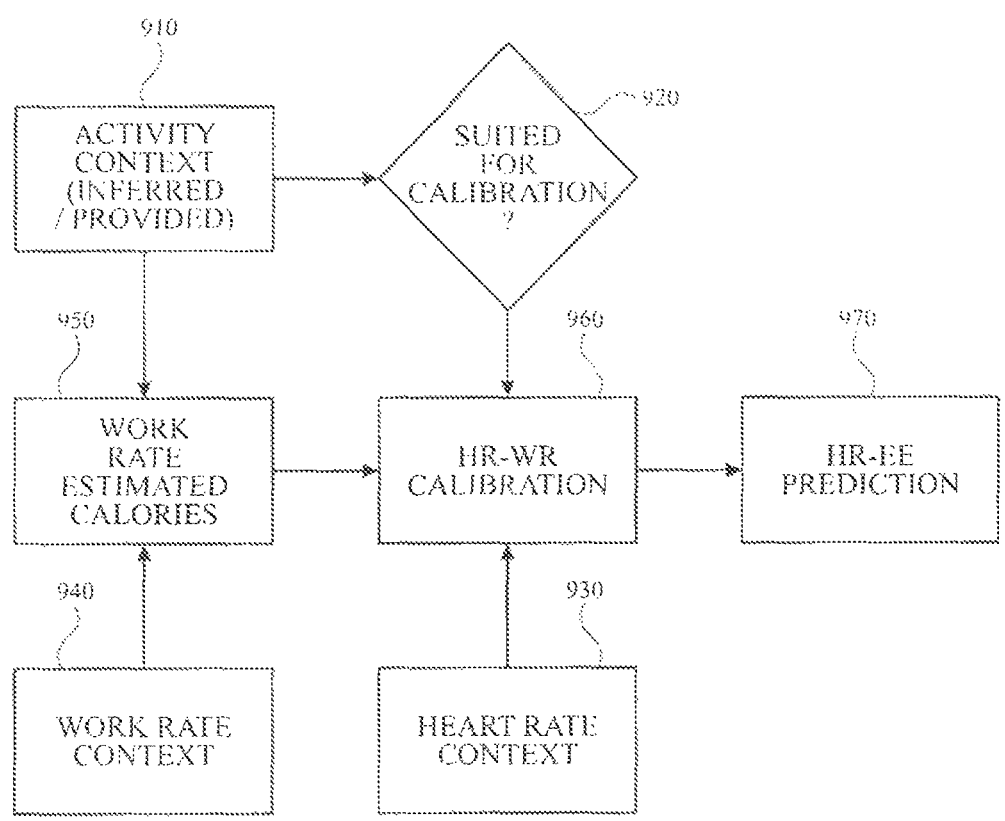
FIG. 9 shows a high-intensity calibration method in accordance with an embodiment of the present disclosure.

In this example, the two-dimensional user-specific table 740 can also account for activity, such as activity type and quantity or mean activity time per day 730, as a way to look at one or more additional variables to break a tie between overlapping ranges. As shown in FIG. 9, a way to distinguish between the minimum steps needed for PAL score 1 (e.g., 1,000 steps for relatively low activity versus 500 steps for relatively high activity) along the second dimension of activity may be to determine, e.g., whether the user walked up at least one flight of stairs. A way to distinguish between overlapping step ranges for PAL score 2 may be to determine, e.g., whether the user spent a (moving daily average) of at least ten minutes on at least one walk or modest bike ride. As another example, a way to distinguish between overlapping step ranges may be to determine, e.g., whether the user spent any time (greater than zero minutes over a moving daily average) on at least one heavy activity, such as a run, bike ride, or other heavy exercise session.

In some embodiments, the two-dimensional user-specific table 740 may use different conditions for distinguishing between relatively low or high activity depending on which PAL scores need to be distinguished (e.g., flights of stairs to distinguish between low PAL scores as opposed to going for a run to distinguish between higher PAL scores). Also, in some embodiments, the two-dimensional user-specific table 740 may include some non-overlapping step minimums or step ranges for which the level of activity or other dimension of data may not affect to the estimated PAL score. For example, in Table III above, if a user reaches approximately at least 6,500 mean steps per day (corresponding to a PAL score of at least 6), the activity metrics may not change the estimated PAL score. In other embodiments, the two-dimensional user-specific table 740 may include overlapping step ranges for every PAL score.

In some cases where step ranges overlap, a user with greater activity time at higher levels of intensity may receive a higher PAL score even if they have fewer total steps than a second user with a lower PAL score. In some embodiments, if a user's activity indicates excessive idle (or sedentary) time, the user may receive a lower PAL score.

As explained above, in some embodiments, accuracy may be improved by configuring the valid day aggregator 520 to determine PAL scores based on moving averages (e.g., a seven-day moving average). Accuracy may also be improved by disregarding days with relatively low total step counts (e.g., days on which the fitness tracking device 100 recorded fewer than 1,000 steps).

Figure 8A:
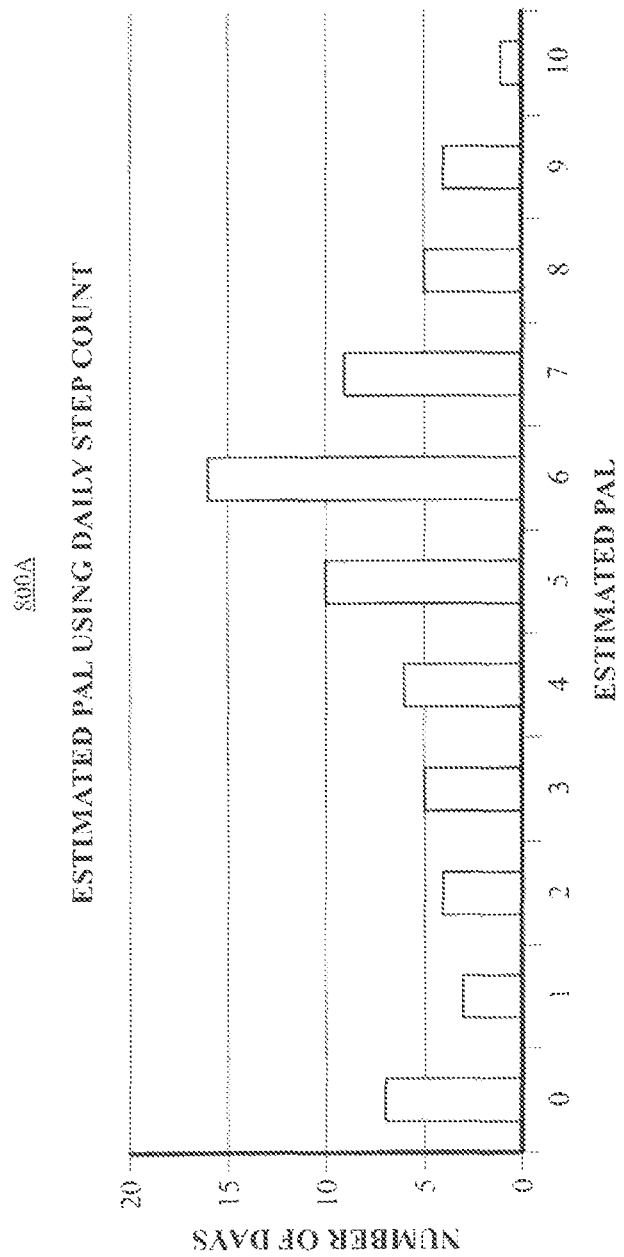
FIGS. 8A-C show chart representations of a calibration technique for inferring physical activity level in accordance with embodiments of the present disclosure.
Figure 8B:
Figure 8C:
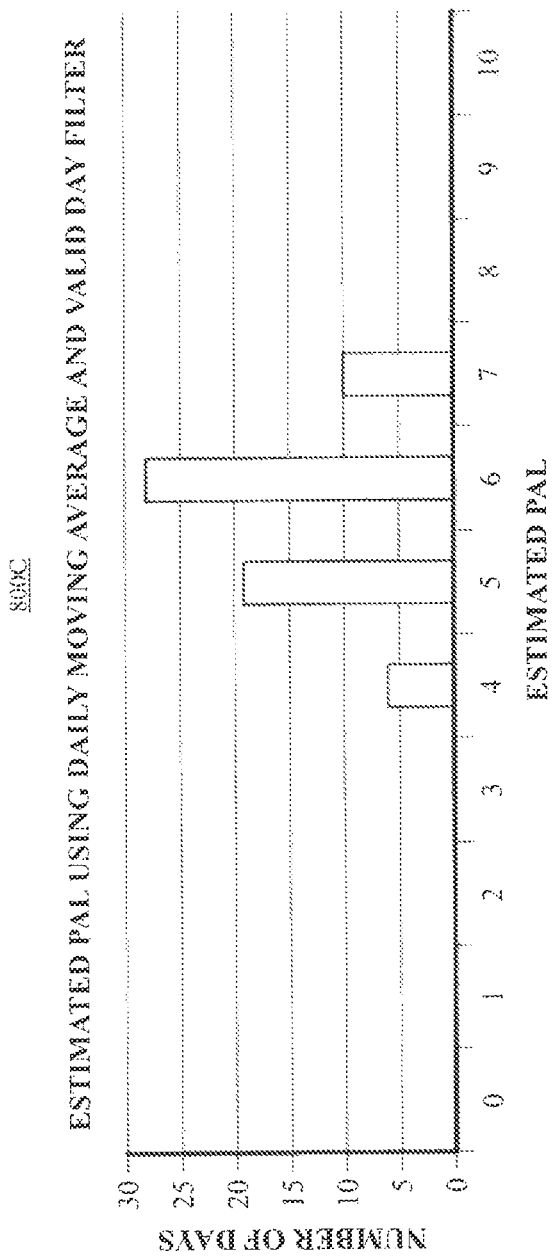

FIGS. 8A-8C illustrate the relative accuracy of different configuration of the valid day aggregator 520 for a hypothetical user whose self-reported PAL (or PA-R) is 6. In this example, the hypothetical user recorded daily total step counts over a 10-week period. Each figure of FIGS. 8A-C includes a histogram (one of charts 800A-C) that illustrates how frequently the calibration technique for inferring a physical activity level would estimate a particular PAL score, given a particular configuration of the valid day aggregator 520 (e.g., daily step count or weekly periodic average). Each chart 800A-C, the same underlying daily step counts are analyzed, but each chart 800A-C applies a different filter to the data, such as daily step count (chart 800A) or a daily moving average (chart 800B).

In FIG. 8A, chart 800A shows the distribution of PAL scores when using a daily step count. Valid day aggregator 520 (e.g., FIG. 5) is either not present, switched off, or otherwise configured to use the daily values of mean steps per day instead of computing a moving average or filtering out low-activity days (i.e., days during which the user may have forgotten to wear the fitness tracking device 100). Chart 800A shows a relatively wide day-to-day variation in PAL scores, including several days rated as "0" when the user may have forgotten to wear the fitness tracking device 100. In some embodiments a PAL score of 0 may be distinguished from days when the device is not worn by estimating a level of, e.g., negative 1. In some embodiments, an individual's physical activity level may be expected to remain relatively constant, but the user's day-to-day activities can fluctuate (e.g., a runner with a self-reported PAL score of 8 may only run every other day). Consequently, this user's daily step count may also fluctuate day-to-day but remain relatively constant over longer time periods.

In FIG. 8B, chart 800B shows the distribution of PAL scores when using a seven-day daily moving average. Charts 800B shows a tighter distribution of estimated PAL scores than chart 800A, and the elimination of some outliers, with the frequency of selecting the self-reported PAL score of 6 (or PAL scores close to 6, e.g., 5) has increased. In some embodiments, the moving average may be computed less frequently. For example, the moving average may be estimated on a weekly basis (e.g., a weekly periodic moving average). In some embodiments, the weekly period moving average may be likely to provide a similar distribution of estimates as the daily moving average example discussed above with reference to FIG. 8B.

In FIG. 8C, chart 800C shows the distribution of PAL scores when the valid day aggregator 520 is not only calculating a daily moving average but also filtering out low-activity days when the user may have forgotten to wear the device. Chart 800C provides the tightest distribution, reflecting the most consistent and accurate estimation of PAL scores compared to charts 800A-C in FIGS. 8A-C.

Calibration—Heart Rate and Work Rate-Based Calibration

Calibration techniques for inferring physical activity level such as those described above may be helpful when exercise-based heart rate or work rate data is not available. Models such as the Jackson et al. model may use physical activity scores such as PAL or PA-R in conjunction with physical characteristics such as age, weight, and sex to estimate aerobic capacity ($\dot{V}O_2$max) without exercising. However, in some cases a user may find that an exercise-based calibration may allow a device such as fitness tracking device 100 to estimate $\dot{V}O_2$max more accurately than the non-exercise or otherwise PAL inference-based calibration techniques such as those described above, and more accurate estimates of $\dot{V}O_2$max may allow for more accurate estimates of energy expenditure when exercising.

In contrast to measuring $\dot{V}O_2$max in a lab setting, $\dot{V}O_2$max can be estimated during suitable "submaximal" exercises (e.g., running for ten minutes). Although the user may not reach maximum aerobic capacity, heart rate or work rate information collected during submaximal testing may allow for the user's $\dot{V}O_2$max to be estimated. Monitoring heart rate measurements (in, e.g., beats per minute or bpm) in conjunction with work rate measurements (in, e.g., joules per second or watts) provides data on which regression analysis may be performed to extrapolate an individual's parameters such as $\dot{V}O_2$max.

In some embodiments, a method for estimating $\dot{V}O_2$max from observations of heart rate and work rate inputs may involve two stages. The first stage may be an estimation process, such as a least squares estimation process, or a running least squares estimation process. In the example of a running least squares estimation process, it may be possible to update the estimate for each new data point without rerunning many prior computations.

The second stage may be a robust outlier rejection strategy, such as a constrained iteratively reweighted least squares solution. In this example, the solution to the estimate may be constrained based on an initial state (e.g., the estimate based on the running least squares estimation process described above). In some embodiments, the constraint may assume that the relationship between heart rate and oxygen consumption is linear. In some embodiments, this assumption of linearity may be extended below conventional thresholds, e.g., the assumption may be extended below a typical assumption of approximately 40%. In some embodiments, the iteratively reweighted solution may seek a minimum $L^p$ norm for, e.g., p=[1.0, 1.5].

In some embodiments, to improve the reliability of data used for calibration, and to filter out some outliers, this calibration method may require one or more conditions to be met. For example, this calibration method may require Fraction of Heart Rate Reserve (FHR) to be less than half (e.g., less than 0.5). FHR may be defined as the ratio of how close an individual's current heart rate is to his or her maximum heart rate (e.g., HRmax−HR) to the individual's heart rate range (e.g., HRmax−HRmin):

$$FHR=(HRmax-HR)/(HRmax-HRmin) \quad (Eq. 2)$$

FHR may range from 0 to 1 for any individual. When an individual's FHR is close to 0, it indicates that the user's heart rate is close to the individual's maximum heart rate. Similarly, when an individual's FHR is close to 1, it indicates that the individual's heart rate is close to the individual's minimum heart rate. Thus, if the individual's FHR is less than 0.5 (i.e., the user's heart rate is closer to maximum heart rate than to minimum heart rate). Consequently, requiring the individual's FHR to be, for example, less than 0.5 may help ensure that the individual is engaged in an active, moderate to high intensity activity that is more likely to be suitable for heart rate and work rate-based calibration.

Similarly, this calibration method may require work-rate based METs to exceed a threshold value (e.g., 5 METs, or 10 METs). Furthermore, in some embodiments, the calibration process may restrict measurements taken while a user is accelerating (e.g., speeding up or slowing down). For example, this calibration method may compare a current measurement of work rate-ba sed METs to a running average or moving average of work rate-based METs (e.g., the change in METs may be required to be with 1 MET of the running average).

In some situations, a user may run at a relatively constant speed and maintain a relatively constant heart rate for the duration of a run. In the absence of any constraints, having approximately one data point, or a tight cluster of similar data points, may not provide enough information to perform a linear regression (e.g., a least squares estimation technique). In some embodiments, the calibration technique may infer at least one additional data point, which may indicate the user's minimum heart rate and basal metabolic rate. Including this inferred data point ensures that: 1) the user's individualized linear heart rate model will include the user's basal metabolic rate at minimum heart rate, and 2) the user's individualized linear heart rate model will have a positive slope within a reasonably constrained range.

In some situations, the user may progress through several local steady states. For example, the user may run at 5 mph for the first five minutes, then speed up to 10 mph for the second five minutes. In this situation, the calibration technique may have at least two reliable data points or clusters of data points with which to perform the least squares estimation process. In some embodiments, the calibration technique will still include the basal metabolic rate and minimum heart rate because it may still be advantageous to ensure the model runs through that point, and it gives the model increased accuracy with yet another data point to include in the regression.

The following section and set of equations indicate how this combined heart rate and work rate-based estimation process may proceed:

Let $h_0$=resting heart rate (or minimum heart rate) of an individual, and let $h_k$, k=1, 2, ..., N denote the obtained heart rate samples, which may be represented by a vector A.

Let $m_0$=the basal metabolic rate estimated for the individual using, e.g., the Mifflin equation, or the Harris-Benedict equation, or an average of the Mifflin and the Harris-Benedict equations. Let $m_k$, for k=1, 2, ..., N denote the work rate-estimated METs obtained at each corresponding time as the heart rate samples, which may be represented by a vector B.

For each heart rate measurement, there is also a weight (e.g., a variance or a confidence level) associated with each heart rate measurement, which may be represented as a diagonal matrix W.

The initial estimate (e.g., the running least squares estimate) may be indicated by $\min\|W(Ax-b)\|_2$, and constrained by $x:[h_0\ 1]x=m_0$, whereby the constraint may compel the least squares estimation to include the point ($h_0$, $m_0$) (the resting heart rate and basal metabolic rate).

This initial estimate based on a running least squares estimation process may be refined further using an iteratively reweighted least squares process. Upon convergence, the user's $\dot{V}O_2$max may be estimated to be $x_1$(HRmax−$h_0$)+$m_0$.

In some embodiments, this $\dot{V}O_2$max may undergo further testing before determining that it should be accepted as a valid calibration. For example, the calibration method may compare the estimated $\dot{V}O_2$max to a ratio of the total METs based on work rate measurements to the % $\dot{V}O_2$max predicted from the heart rate measurements, whereby % $\dot{V}O_2$max=f(FHR), and where f(x) is a machine-learned algorithm for predicting % $\dot{V}O_2$max from FHR. This ratio is effectively another estimate of $\dot{V}O_2$max. If the divergence between the HR-WR based $\dot{V}O_2$max is within a threshold of the ratio estimate of $\dot{V}O_2$max, the HR-WR based $\dot{V}O_2$max may be accepted as the user's (calibrated) $\dot{V}O_2$max.

In some embodiments, this divergence process may be used to compare a subsequently estimated $\dot{V}O_2$max to a previously accepted $\dot{V}O_2$max. If the two values are within a threshold divergence of one another, it may be assumed that the previously estimated $\dot{V}O_2$max was valid. In a situation in which the new $\dot{V}O_2$max has diverged from the previous $\dot{V}O_2$max beyond a threshold divergence, it may be an indication that the user's $\dot{V}O_2$max has changed, and the new $\dot{V}O_2$max may be accepted as a recalibrated value.

As explained below, the fitness tracking device 100 may further be able to take into account data such as automatic activity classification data, user input about when a user is beginning or ending an exercise session and what type of exercise (e.g., running or cycling) the user will be performing, and sensor information from other devices such as GPS location data from the companion device 300 via interface module 240 (FIG. 2).

FIG. 9 shows a high-intensity calibration method in accordance with an embodiment of the present disclosure. At block 910, an activity context may be inferred or provided. For example, in some embodiments, an activity classifier may automatically detect the type of activity (i.e., activity context) that a user is performing. In other embodiments, the fitness tracking device 100 may be configured to receive information from the user about the activity context that the user is performing or intends to begin performing (e.g., the user indicates that the user is "in session" for running) Once an activity context has been inferred, provided, or otherwise detected, the method may proceed to block 920.

At block 920, a determination is made as to whether the previously determined activity context may be suitable for HR-WR calibration (960). For example, HR-WR calibration 960 may be most accurate for vigorous, intense exercises, such as running for at least ten minutes.

For a given time period, the inferred activity context may not be able to predict whether a context that is suitable for calibration may be interrupted before enough time has elapsed or enough HR-WR data has been collected to calibrate accurately. Thus, the activity context may be inferred continuously, or at periodic intervals, at block 910 to detect whether the activity context may have changed. If a change is detected, and it is determined at block 920 that the new activity context is not suitable for HR-WR calibration 960, the calibration method may abort or restart.

At block 930, heart rate context may be obtained continuously or at periodic intervals (e.g., once per minute, or once per three minutes, etc.). For example, the fitness tracking device 100 may obtain a heart rate context by receiving heart rate data from a PPG sensor in the heart rate sensing module 220 (FIG. 2). In some embodiments, the frequency for checking the user's heart rate may be increased if the activity context indicates that the user is performing an activity suitable for HR-WR calibration 960. A confidence level for a heart rate measurement at a given time period may also be determined to facilitate HR-WR calibration 960.

At block 940, work rate context may be obtained continuously or at periodic intervals (e.g., once per minute, or once per three minutes, etc.). For example, the fitness tracking device 100 may obtain motion data from an accelerometer or other sensor in motion sensing module 230 (FIG. 2). In some embodiments, work rate context may also be derived using altitude information from an altimeter or location information from a GPS sensor, and these sensors may optionally be located in a companion device 300 that is also strapped or otherwise worn by the user during the intense calibration activity. For example, while running or cycling, GPS information may convey a distance traversed to assess the user's speed. Similarly, altimeter information may convey information about changes in grade to assess the power needed to traverse a given distance at a given grade.

In other embodiments, the fitness tracking device 100 may be configured to receive annotations of the work in watts. For example, if the user is exercising on a stationary bike, GPS information will not be useful for determining work rate. Additionally, if the stationary bike simulates changes in grade, altimeter information will not be useful for determining changes in work rate due to changes in grade. Thus, in a graded stationary cycling calibration activity, during which GPS and altimeter information may not be useful, watt annotation from the user may be useful.

At block 950 a calorimetry process may be performed to estimate calories burned based on the work rate data from the work rate context from block 940. The work rate model applied for the work rate calorimetry process at block 950 may vary depending on the received activity context. For example, the work rate calorimetry model for running may be different from the work rate model for cycling, as described in more detail herein.

At block 960, HR-WR calibration may be performed if there is an indication from block 920 that the current activity context is suitable for calibration. HR-WR calibration 960 may use both the heart rate context from block 930 and the work rate estimated calories information from block 950 (which was based on the motion and other data from the work rate context determined at block 940 and the activity context determined at block 910).

At block 970, the conclusion of the intense activity suited for calibration, and if the intense activity endured sufficiently long (e.g., a ten-minute run) to collect sufficient heart rate or work rate data to estimate $\dot{V}O_2max$ as explained above, the estimated $\dot{V}O_2max$ may be used to generate a model for energy expenditure based on the linear relationship between heart rate and $\dot{V}O_2$ described above. This energy expenditure model may be more accurate than a model determined based on heart-rate measurements alone without the benefit of work rate measurements, especially for heart rate data for time periods when the confidence level is relatively low. This heart-rate energy expenditure model estimates a user's $\dot{V}O_2max$ to be used by subsequent calorimetry processes. Additionally, these parameters may be estimated more accurately than the low-intensity, non-exercise based calibration, which estimates physical activity level to estimate $\dot{V}O_2max$ instead of heart rate and work rate measurements during exercise.

This process may also be repeated to recalibrate or refine the calibration of the energy expenditure model by initiating another intense activity suited for calibration.

By generating a more accurate calorimetry model to estimate energy expenditure using heart rate (or a combination of heart rate and work rate) during exercise, the fitness tracking device 100 may be configured to provide the user with a more accurate estimate of calories burned during exercise, which in turn provides the user with a more accurate estimate of total energy expenditure throughout the day over a variety of activities.

Calorimetry—Overview

Once a device such as the fitness tracking device 100 has been calibrated, it may perform calorimetry, i.e., measuring a user's energy expenditure (e.g., calorie burn) over time and across a variety of activities. Because the fitness tracking device 100 may be configured with a default calibration (i.e., a default PAL score combined with physical characteristics that may be provided during a brief setup or initialization phase), the fitness tracking device 100 may begin tracking energy expenditure immediately or nearly immediately.

The fitness of the user may change over time, the device may be recalibrated, or the calibration of the device may be refined (e.g., by processes described above, such as a calibration technique for inferring physical activity level, or an active work rate and heart rate-based calibration technique). As the fitness tracking device 100 refines and improves upon its understanding of the user's individualized characteristics, such as estimates for maximum heart rate and $\dot{V}O_2max$, the calorimetry processes of the fitness tracking device 100 may become increasingly accurate over time, and remain accurate even if the user's fitness level changes over time as well.

Developing a heart rate-based energy expenditure model may be helpful for calorimetry processes that measure energy expenditure for moderate to vigorous activities. Even in these cases, an algorithm or model that works well for running may not work as well for cycling (e.g., the METs for running may be different from the METs for cycling). Additionally, some activities may rely more on work rate calculations or a combination of work rate calculations with heart rate monitoring. The following section describes in detail various embodiments in which calorimetry processes may use a fusion of heart rate and work rate data to estimate energy expenditure more accurately across different activities such as running and cycling.

For some activities, such as using elliptical trainers or step machines, which provide a load or resistance that affects energy expenditure, individuals may experience an elevated heart rate as the resistance of the machine increases. The sections that follow also describe accurate heart-rate based calorimetry models based on an estimated load.

For some activities, such as weight lifting, which are not paced activities such as running, individuals may experience frequent changes in heart rate as they engage in the onset of an activities (e.g., an individual repetition or a set of repetitions), and cool-down periods (e.g., moments of time between repetitions or a brief rest between sets of repetitions). The sections that follow also describe accurate heart rate-based calorimetry models for intermittent activities.

For other, lower heart-rate activities, such as walking, a heart rate-based calorimetry model may not be as reliable as some other methods. For these activities, a pedometry-based calorimetry model and process may be more accurate or more reliable.

Additionally, users also burn calories while sedentary (e.g., sleeping, sitting, standing, or otherwise "at rest"). However, the energy expenditures vary among these activities and across individuals (e.g., sitting requires fewer METs than standing). Especially for users who may spend a substantial portion of their day sitting (or standing), accurate day-long calorimetry processes may benefit from being able to distinguish between whether a user is sitting or standing automatically, and adjust the calorimetry model accordingly. Even a relatively small difference in METs between sitting and standing may add up to be a substantial difference in energy expenditure over the course of a day for a relatively sedentary individual.

Calorimetry—Heart Rate and Work Rate-Based calorimetry

As explained below with reference to FIG. 10, and similar to heart rate and work rate-based calibration described above with reference to FIG. 9, combining heart rate and work rate information may provide more accurate calorimetry than either method on its own.

Figure 10:
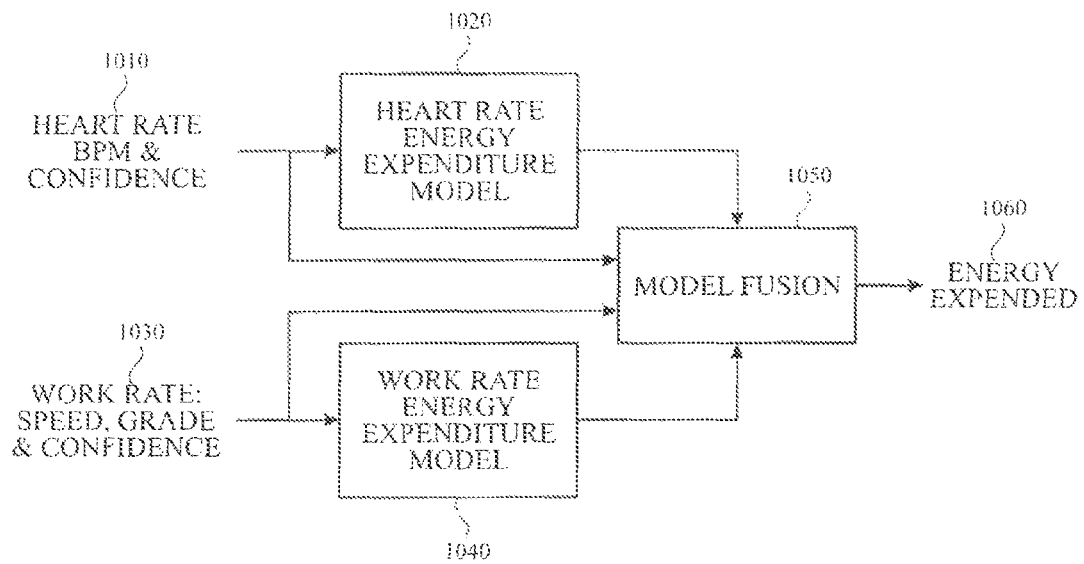
FIG. 10 shows a high-intensity calorimetry method in accordance with an embodiment of the present disclosure.

FIG. 10 shows a high-intensity calorimetry method in accordance with an embodiment of the present disclosure. At block 1010, a current heart rate (e.g., beats/min) may be obtained from the heart rate sensing module 210 (FIG. 2).

In addition to providing the current heart rate, the heart rate sensing module 210 may also provide a confidence level (e.g., $\sigma^2_{HR}$) associated with the current heart rate. The confidence level is a quantified indicator of how accurate the heart rate sensing module 210 may be. For example, if the heart rate sensor input is relatively noisy, the confidence level for the measured heart rate may be relatively low. In some embodiments, the confidence level originating from the heart rate sensor (e.g., a PPG sensor) may be adjusted depending on other measured conditions. For example, if it is known that heart rate sensor values are relatively noisy at higher speeds, such a property may be incorporated into the computation of the confidence time series.

The current heart rate and confidence level may be used to compute a normalized heart rate (NHR), (or fraction of heart rate reserve (FHR), as explained above):

$$NHR = (HR_{max} - HR)/(HR_{max} - HR_{min}) \quad \text{(Eq. 2A)}$$

NHR may be used as an input to a heart-rate based calorimetry model during exercise to estimate the current (or "instantaneous") rate of energy expenditure (or calorie burn) during exercise.

The individualized values for minimum and maximum heart rate and $HR_{min}$ and $HR_{max}$) may have been previously estimated using one of the previously described calibration techniques. At block 1020, an estimate of energy expenditure based on a heart rate model may take NHR as input and output the user's corresponding percentage of aerobic capacity (% $\dot{V}O_2$max). Because the user's individualized $\dot{V}O_2$max may have been previously estimated using one of the previously described calibration techniques, the heart rate model may convert % $\dot{V}O_2$max into METs and calories burned (i.e., energy expended) according to the heart rate data.

Similarly, at block 1030, the work rate may be estimated using motion data or related information. A confidence level for work rate may also be computed (e.g., $\sigma^2_{WR}$). In some embodiments, work rate confidence may be determined based on a relative accuracy of a GPS sensor for a given piece location information. In some embodiments, a GPS sensor may be included in the companion device 300 but not the fitness tracking device 100. If the companion device 300 is not available to communicate GPS sensor information to the fitness tracking device 100, heart rate and work rate confidence information (e.g., heart rate and work rate variances) may not be available to apply a mixing function (e.g., a weighted, probabilistic average of heart rate and work rate based on their relative variances), which is explained in more detail below in reference to Equation 9.

At block 1040, an estimate of energy expenditure based on a work rate model and predetermined activity context may output calories burned (i.e., energy expended) according to the work rate data.

At block 1050, the heart rate-based energy expenditure ($EE_{HR}$) may be "fused" or otherwise combined with the work rate-based energy expenditure ($EE_{WR}$). In some embodiments, the data may be fused using a Bayesian probability framework. For example, the framework may be expressed as determining the best estimate for energy expenditure (EE), given the work rate and heart rate estimates $EE_{HR}$ and $EE_{WR}$:

$$\begin{aligned} P(EE | EE_{HR}, EE_{WR}) &= P(EE_{HR}, EE_{WR} | EE)P(EE) / \\ &\quad P(EE_{HR}, EE_{WR}) \\ &= P(EE_{HR}, EE)P(EE_{WR}, EE)P(EE) / \\ &\quad P(EE_{HR}, EE_{WR}) \end{aligned} \quad \text{(Eq. 2B)}$$

The Bayesian framework expressed in Equation 6 assumes that the output of the heart rate and work rate models are independent. If a uniform prior and normal densities are assumed for the following likelihood functions . . .

$$P(EE_{HR}) \sim N(EE, \sigma^2_{HR}) \quad \text{(Eq. 2C)}$$

$$P(EE_{WR}) \sim N(EE, \sigma^2_{WR}) \quad \text{(Eq. 2D)}$$

. . . then the maximum a posteriori estimate for EE may be given by the following "mixing function":

$$EE = (\sigma^2_{HR} EE_{WR} + U_{WR} EE_{HR}) / (\sigma^2_{HR} + \sigma^2_{WR}) \quad \text{(Eq. 2E)}$$

The variances $\sigma^2_{HR}$ and $\sigma^2_{WR}$ may correspond to the confidence values for the heart rate input from block 1010 and the work rate input from block 1030, respectively. A decrease in the variance from one sensor (i.e., an increase in confidence) may cause the fused estimate of EE computed with Equation 9 to tend toward the value of the sensor with the decreased variance.

At block 1060, the energy expenditure estimate EE computed using the mixing function at Equation 2E may be outputted.

Calorimetry—Heart Rate and Work Rate-Based Calorimetry for Cycling

As mentioned above, the work rate energy expenditure model used at block 1040 may depend in part on the type activity (e.g., activity classification). For example, in the case of cycling, an accurate work rate model may be based on a nonlinear combination of speed and grade. This model may estimate the total energy expended EE by estimating an amount of energy required to move a cyclist (e.g., the user while cycling) through space.

The main sources of resistance are defined by the rolling resistance ($P_{rr}$), aerodynamic drag ($P_{ad}$), changes in potential energy ($P_{pot}$), and changes in kinetic energy ($P_{kin}$):

$$P_{rr} = V_g C_{rr} mg \cos(\arctan(G)) \quad \text{(Eq. 3A)}$$

$$P_{ad} = \beta(T) C_\alpha (V_g + V_w \cos(\alpha))^2 V_g \quad \text{(Eq. 3B)}$$

$$P_{pot} = V_g mg \sin(\arctan(G)) \quad \text{(Eq. 3C)}$$

$$P_{kin} = 0.5(m + I/r^2)(V^2_{gf} - V^2_{gi})/(t_f - t_i) \quad \text{(Eq. 3D)}$$

$$P_{total} = P_{rr} + P_{ad} + P_{pot} + P_{kin} \quad \text{(Eq. 3E)}$$

In Equations 3A-E:

$V_g$ is the ground speed of the cyclist, which in some embodiments may be determined based on GPS sensor data.

$C_{rr}$ is the coefficient of rolling resistance, which in some embodiments may be assigned a default value.

m is the combined mass of the bike and the cyclist. In some embodiments, the mass of the bike may be assigned a default value, and the mass of the cyclist may be determined based on the user's weight.

g is gravity, which may be assigned a default value of $g_n$, the "standard" or average gravity at the Earth's surface (i.e., 9.80665 m/s$^2$).

G is the slope of the surface. In some embodiments, a default value (e.g., 0 radians) may be assigned. In other embodiments, data from one or more motion sensors (e.g., an altimeter) may be used to estimate a current slope of the surface.

$\rho(T)$ is a temperature-dependent air density. In some embodiments, a default value (e.g., an average temperature) may be assigned. In other embodiments, the fitness tracking device 100 or the companion device 300 may be configured to obtain a current temperature value for the user's location (e.g., GPS sensor-based location). In other embodiments, the fitness tracking device 100 or the companion device 300 may include a temperature sensor.

$C_\alpha$ is the constant for aerodynamic drag, which may be assigned a default value.

$V_w$ is the wind speed, and $\alpha$ is the angle between the wind vector and the cyclist's direction of travel or speed (e.g., the cyclist's velocity vector). In some embodiments, $V_w$ and $\alpha$ may be assigned default values. In other embodiments, the fitness tracking device 100 or the companion device 300 may be configured to compute these parameters by obtaining a current wind speed and a current wind direction for the user's location, as well as the cyclist's current direction of travel.

I is the moment of inertia of the wheels on cyclist's bike. In some embodiments, I may be assigned a default value.

r is the radius of the wheel. In some embodiments, r may be assigned a default value.

$V_{gf}$ and $V_{gi}$ correspond to the final and initial velocities, respectively, when the cyclist accelerates.

These factors should not be considered exhaustive. Examples of other factors for which some embodiments may account in their models include drive train losses, wheel bearing losses, and wheel rotation.

The actual energy expended by the cyclist may also depend on their bio-mechanical efficiency ($\eta$):

$$EE = \eta \cdot P_{total} \quad \text{(Eq. 3F)}$$

In a case where not all of the constants are known, the model may be approximated by:

$$EE = V_g(\alpha_1) mg \cos(\arctan(G)) + (\alpha_2) V_g + (\alpha_3) V_g^2 + (\alpha_4) V_g^3 + (\alpha_5) V_g mg \sin(\arctan(G)) + (\alpha_6) m(V^2_{gf} - V^2_{gi})/(t_f - t_i) \quad \text{(Eq. 3G)}$$

In some embodiments, coefficients $\alpha_1$-$\alpha_5$ may be learned from a training set.

In some embodiments, additional improvements may be made to improve the accuracy of the heart rate model or the work rate model. For example, temporal dynamics (e.g., a Kalman filter), or a determination of a regression function from the data using a more general model such as a random forest or a neural network, may be applied the either or both of the heart rate model and the work rate model.

Calorimetry—Automatic Terrain Detection

Another example where additional improvements may be made to the cycling work rate model (and, in some embodiments, a pedestrian or running work rate model, etc.) is with a method for automatic terrain detection. For example, being able to distinguish between different types of terrain (e.g., cement, asphalt, dirt, gravel, etc.) may allow for updating the cycling work rate energy expenditure model to use a more accurate value for certain parameters, e.g., the coefficient of rolling resistance ($C_{rr}$), which may allow for a more accurate estimate of rolling resistance ($P_{rr}$), which, in turn, may allow for more accurate estimate of energy expenditure while cycling on a particular type of terrain.

In some embodiments, automatic terrain detection may also improve the work rate model for pedestrian activities (e.g., running) by allowing the work rate expenditure model to include an additional efficiency parameter related to terrain. For example, some terrain types (or types of surfaces) are easier to run on than others and may be more efficient. For example, a track may require less energy to maintain a given speed than, e.g., a gravel trail. The efficiency of a given terrain in the context of running (or a comparable activity) may be expressed as an efficiency (or "correction") term, such as a linear correction factor such as (a)(EE)+(b). In this example, determining the terrain may allow values for the (a) and (b) parameters (multiplicative and additive factors, respectively) to be inferred as well.

Figure 11:
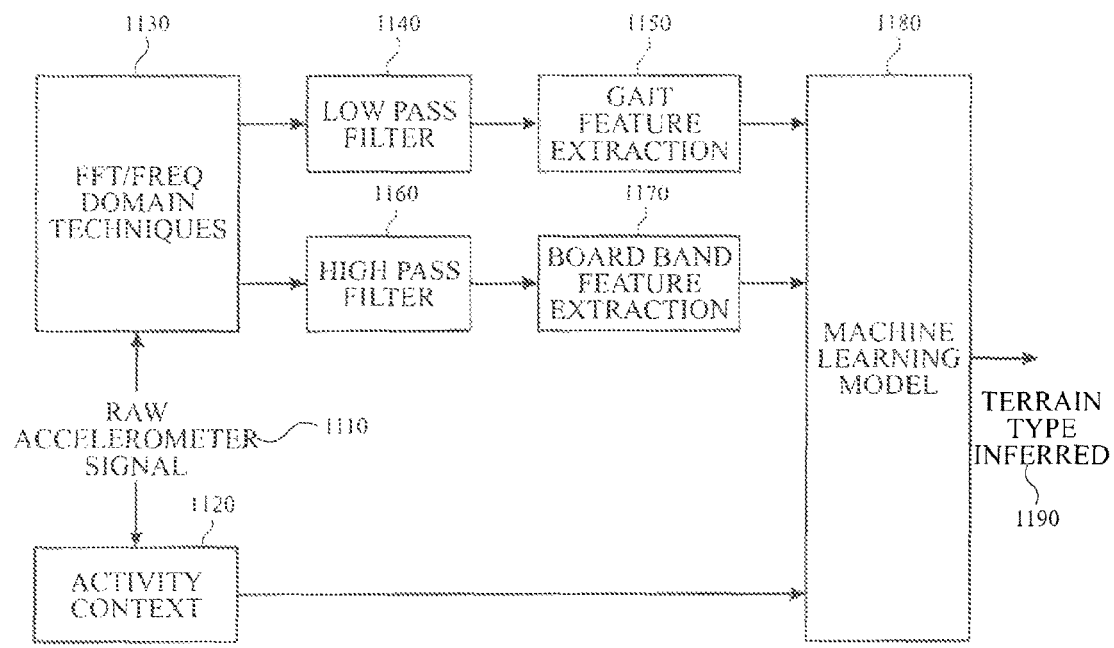
FIG. 11 depicts a terrain detection method in accordance with an embodiment of the present disclosure.

FIG. 11 depicts a terrain detection method in accordance with an embodiment of the present disclosure. At block 1110, a "raw" accelerometer signal is provided to both block 1120 for determining an activity context and block 1130 for performing Fast Fourier Transforms (FFTs) and frequency domain analysis. Because the accelerometer signal is "raw," meaning that the signal has not been filtered or processed yet, a full frequency spectrum in the signal may be available for analysis. The raw accelerometer signal may be provided from an accelerometer included in the motion sensing module 220 (FIG. 2) of the fitness tracking device 100.

At block 1120 an activity context may be determined based on the raw accelerometer signal from block 1110. In some embodiments, the raw accelerometer signal may be analyzed to determine the activity context (e.g., running or cycling). In other embodiments, the fitness tracking device 100 may receive input from a user about the type of session activity that the user may be performing. As explained in more detail below, the activity context information may be used at block 1180 to help infer the terrain type automatically, which may be performed based on a machine learning model.

At block 1130, the raw accelerometer signal from block 1110 may be transformed to the frequency domain (e.g., with an FFT algorithm).

At block 1140, a low-pass filter (LPF) may be applied to the accelerometer signal in the frequency domain. The LPF may be configured to extract a "gait feature" at block 1150. The gait feature may be the portion of the frequency spectrum in the motion data from a human source, as opposed to portions of the frequency spectrum that represent noise such as vibrations due to different types of terrain. The gait feature may appear as the dominant frequency at, for example, up to 4 Hz, or up to 5 Hz. By subtracting the gait feature frequency range from the motion data (e.g., by performing source separation on the motion data), the machine learning model may be applied at block 1180 to detect the type of terrain automatically with greater accuracy.

Similarly, at block 1160, a high-pass filter (HPF) or a band-pass filter may be applied to the accelerometer signal in the frequency domain. The HPF may be configured to extract broad band features from the frequency spectrum at block 1170, which may contribute to inferring the terrain type by the machine learning model at block 1180. For example, the broad band features from the frequency spectrum may include the residual noise in, e.g., the 5-20 Hz range, or the 7-25 Hz range, etc.

In addition to the residual noise at higher frequencies that may be attributable to the terrain, there may also be residual harmonics at higher frequencies that may be attributable to the (lower-frequency) gait feature. In this example, information about the gait feature obtained with the LPF may be used to subtract at least some of the residual harmonics due to the gait feature from the higher-frequencies obtained by the HPF.

At block 1180, the terrain type may be inferred using a machine learning model that accounts for activity context from block 1120, the gait feature frequency information from block 1150, and the broad band frequency information from block 1170. In some embodiments, the gait feature may represent a frequency signature attributable to the user's activity. After the frequency signature attributable to the user's activity has been subtracted out, the residual frequency spectrum may consist of noise induced by the terrain. The broad band frequency spectrum may exhibit recognizable characteristics for recognizing different types of terrain.

In some embodiments, the high-pass filtering, broad band feature extraction, or machine learning model may leverage existing processes performed for activity context. For example, the same broad band road noise features that may be used by the activity context classification process to identify a cycling activity context may also be used to determine the type of terrain on which the user is cycling.

Also, in some embodiments, the machine learning model may benefit from a fitness tracking device 100 that is worn on the user's wrist. For example, during a cycling activity, energy transferred from the terrain through the handlebars to the user's hands may reach the user's wrist more reliably that if a device with an accelerometer were positioned farther away from the user's hands.

Calorimetry—Automatic Load Estimation

For certain types of activities, such as indoor exercise sessions (on, e.g., elliptical trainers, rowing machines, stepper machines, etc.), calorimetry accuracy may be improved by automatically estimating load (or "mechanical resistance") from the equipment. For example, many elliptical trainers may have a configurable load or resistance that allows the user to adjust how much effort is needed to perform each repetition on the machine. The higher the load, the more effort is needed, and therefore the energy expended to perform the work also increases.

For example, energy expenditure on an elliptical trainer may be modeled using the following equation:

$$\text{Elliptical Energy Expenditure} = (a)(\text{counts/min}) + (b)(\text{counts/min})(\text{load}) + (c) \quad \text{(Eq. 4A)}$$

In Equation 16A, (a)-(c) are parameters that may be calibrated or otherwise adjusted for an individual user. Counts per minute ("counts/min") represents the number of revolutions of an elliptical trainer. In other models, e.g., for other types of equipment or exercises, the model may include a variable for step rate, stroke rate, etc. "Load" represents the amount of resistance that the elliptical trainer (or other exercise equipment) is configured to provide to increase the difficulty of the workout. For example, in the case of a treadmill, estimated load may represent an angle of incline (or grade or gradient) of the treadmill. As the incline of the treadmill increases, the user may need to expend more energy to maintain the same speed.

In some embodiments, at the beginning of a workout session (e.g., an elliptical trainer exercise session), the initial load may be set to a default value. As explained below, during the workout, e.g., during an "acquisition" phase, the default load value may be adjusted to an estimated load value based on a combination of a measured work rate (e.g., step rate) and a measured heart rate.

In some embodiments, heart rate measurements may not be available for all time periods during a workout. For example, the fitness tracking device 100 may reduce the frequency for measuring heart rate to conserve battery power, or a particular attempt to measure heart rate may produce a noisy result with a low confidence (e.g., high variance). In some embodiments, if a relatively reliable (high confidence) heart rate measurement is available, it may be used to update the estimated load for a given time period or for a subsequent time period. However, if no heart rate measurement is available, or if only a relatively unreliable (low confidence) heart rate measurement is available, the previously estimated load (or default load) may be used to estimate energy expenditure for the given time period or for a subsequent time period.

In some embodiments, heart rate measurements may only be made opportunistically, during opportunities for more accurate acquisition of an estimated load. For example, if a user's step count is changing, it may be an indication that a user is accelerating, e.g., at the beginning of a workout or interval, in response to adjusting a resistance of the equipment, or at the end of a workout or interval. In some embodiments, load estimation may be more accurate during a time period in which the user's step count is relatively steady, because a steady step count may be an indication that the user has set a pace for a given resistance level, which in turn may allow for more accurate estimation of the given resistance level.

Figure 12:
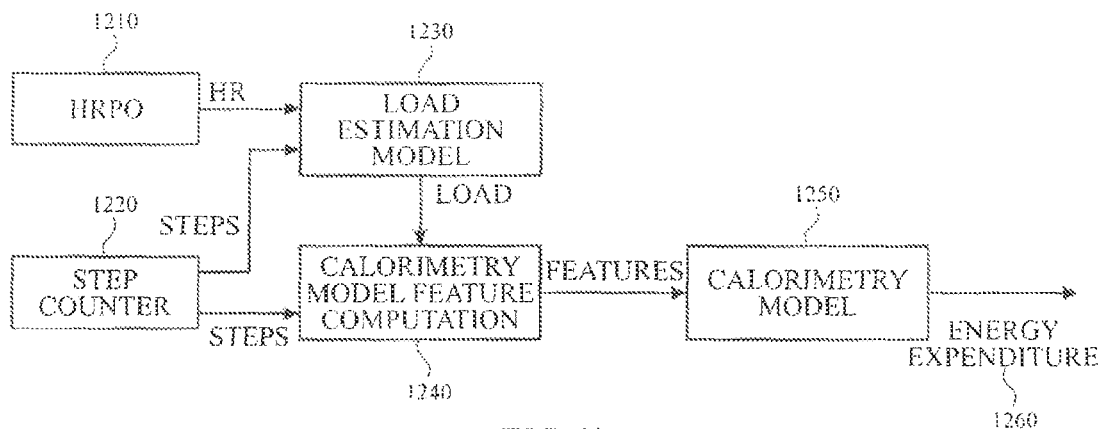
FIG. 12 shows a load estimation method in accordance with an embodiment of the present disclosure.

FIG. 12 shows a method for automatic load estimation based on an embodiment of the present disclosure. As show in FIG. 12, a heart rate ("HR") may be provided by, e.g., a heart rate sensor of the fitness tracking device 100 at block 1210 ("Heart Rate Path Optimization"). The heart rate provides a first indication of how hard a user is working. For example, as load increases, the user's heart rate may also increase.

Additionally, as shown in FIG. 12, a step rate ("Steps") may be provided by, e.g., a pedometer function of the fitness tracking device 100 at block 1220 ("Step Counter"). The step rate, which is an indication of the user's work rate, provides a second indication of how hard a user is working. For example, as load increases, the user may need to expend additional energy to maintain a steady step rate (or work rate).

At block 1230 ("Load Estimation Model"), the heart rate may be received from block 1210, and the step rate may be received from block 1220. As explained in detail below with reference to FIG. 13, a model for estimating load may be applied at block 1230. The estimated load may be output from block 1230.

At block 1240 ("Calorimetry Model Feature Computation"), the load estimate may be received from block 1230, and the step rate may be received from block 1240. For example, the step rate may be used to determine the "counts/min") input for Equation 4A for computing elliptical trainer energy expenditure. At block 1240, features related to the calorimetry model may be computed based on the estimated load and step rate. In the example of the elliptical trainer, a counts/min feature may be outputted from block 1240, and a feature representing the product of the counts/min and the estimated load may also be outputted from block 1240.

At block 1250 ("Calorimetry Model"), one or more features may be received from block 1240. In the example of the elliptical trainer, features representing both the counts/min and the counts/min times estimated load may be received at block 1240. These features may be applied to a calorimetry model (e.g., an individually parameterized model indicated by Equation 16A) to estimate energy expenditure (2260).

Figure 13:
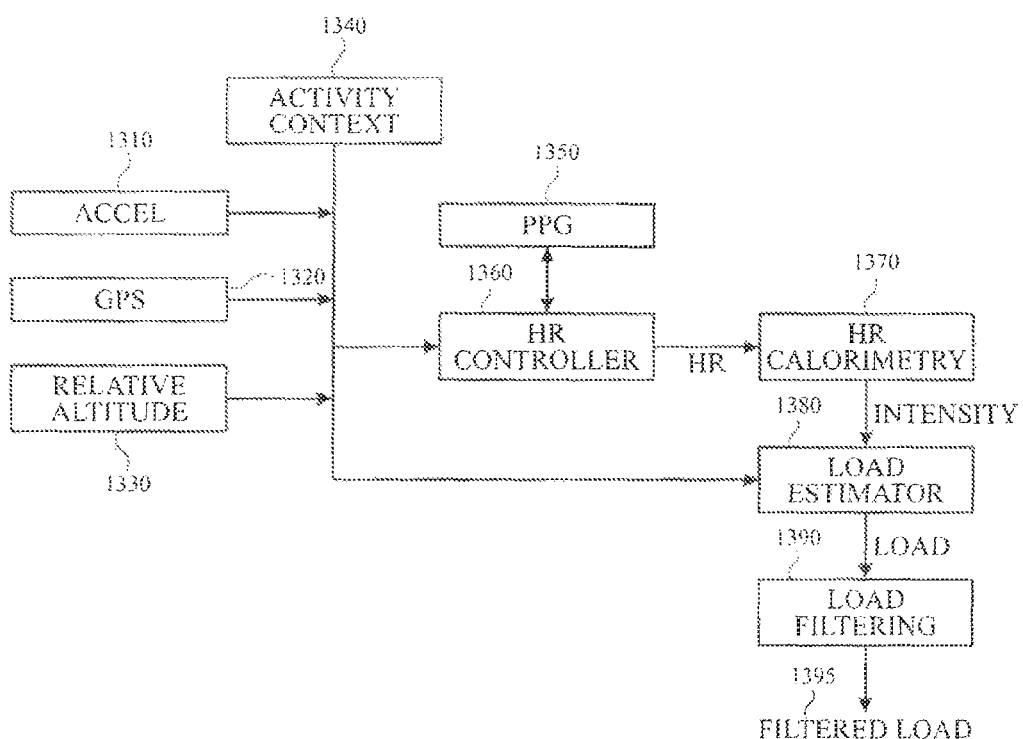
FIG. 13 shows a load estimation method in accordance with an embodiment of the present disclosure.

FIG. 13 shows additional details of an automatic load estimation method, such as the automatic load estimation method described above with reference to FIG. 12. As shown in FIG. 13, several sensors from the fitness tracking device 100 or the companion device 300 may provide motion data or other information to improve the accuracy of the load estimation method.

For example, accelerometer data may be provided by an accelerometer at block 1310. In some embodiments, the pedometer functionality such as the step counter for determining step rate may be implemented or otherwise determined from accelerometer motion data.

In addition to accelerometer data, GPS data may be provided by a GPS sensor (block 1320) and relative altitude information may be provided by an altimeter (block 1330).

At block 1340, an activity context may be provided, which may indicate that the user is in, for example, an elliptical trainer exercise session. In some embodiments, the activity context may be inferred or otherwise determined by an activity classifier function based on motion data or other information. In some embodiments, the activity context may be determined based on user input. For example, the user may indicate to the fitness tracking device that the user is about to begin an elliptical training exercise session.

At block 1350, a heart rate sensor, such as a PPG sensor, of the fitness tracking device 100 may be provide heart rate information to a heart rate controller at block 1360.

At block 1360, the heart rate controller may also receive activity context information from block 1340. For example, if the activity context indicates that the user indicated to the device that the user is "in session," the heart rate controller may request heart rate information relatively frequently (e.g., once per minute). However, in some embodiments, if the activity context indicates that the user's in-session status has been inferred based on motion data, the heart rate controller may sample heart rate information relatively less frequently (e.g., once per three minutes) to conserve battery power.

At block 1370, a heart-rate based calorimetry model may be applied using the heart rate from block 1360 as an input and providing a heart-rate based intensity (e.g., estimated $\dot{V}O_2$) to block 1380.

At block 1380, an estimated heart-rate based intensity may be received from block 1370, and work rate information based on motion or activity data may be received from at least one of blocks 1310, 1320, 1330, and 1340. The load estimator may apply, e.g., a regression analysis or a decision tree analysis to the heart-rate based intensity and step rate inputs (e.g., a "load estimation model" as described above with reference to FIG. 12 at block 1230). For example, a relatively high heart rate for a given step rate may indicate a relatively high load. The estimated load for a given time period may be output from block 1380.

In some embodiments, the load estimation model may account for the activity context. For example, in some activities, load or resistance may be a scaling factor for another variable such as speed. Also, in some embodiments, the load estimation model may account for whether other factors may be estimated through other techniques, or whether they may be accounted for by the load estimate. For example, if a user is running with access to altimeter data (e.g., from the companion device 300), the load may be estimated separately from the grade factor. However, if altimeter data is not available, the load estimate may be determined to account for variations in energy expenditure due to grade as well.

In some embodiments, load filtering may be applied at block 1390. The estimated load for the given time period may be received from block 1380. The load may be filtered using historical estimated load values (e.g., hysteresis) to smooth load estimation. For example, a load filter may limit the amount by which an estimated load may change from one time period to the next. The filtered load estimate (2395) may be out output.

In some embodiments, this technique may also be applied to various outdoor activities (e.g., running, walking, cycling). In these activities, estimated load may be used to estimate other variables in the models for these activities that affect the amount of effort that is needed to, e.g., run or pedal a bicycle. For example, the width of the tires on a bicycle, the selected gear of the bicycle, the type of the terrain, grade of the terrain, and wind speed are some of the factors that may affect the total load or resistance for these activities.

For example, energy expenditure based on speed may be applied to activities such running and cycling:

Running/Cycling Intensity=$(a)$(speed)+$(b)$(speed) (grade)+$(c)$  (Eq. 4B) (See also Eq. 6A, below)

In Equation 4B, (a)-(c) are parameters that may be calibrated on an individualized basis, and grade may be approximated using estimated load.

Calorimetry for Intermittent Activity

High-intensity, short-duration activities (e.g., cross-fit training, interval running, etc.) are becoming increasingly popular techniques for training goals such as cardiorespiratory fitness, strength, weight loss, etc. These activities are often "untyped," or at least complex to type, which may cause it to be more difficult to classify these activities automatically. For example, interval running may appear to be similar to running during onset of a high heart rate.

Unlike a more conventional running activity—during which the user may have a brief onset period, followed by an extended amount of time spent running with an elevated heart rate, and concluded by a cool-down period—interval running has relatively short periods of time spent running with an elevated heart rate, punctuated with frequent transitions between periods of onset and cool-down. Thus, by combining calorimetry processes that may be configured to be accurate for onset detection, active hart-rate calorimetry, and passive cool-down calorimetry, the fitness tracking device 100 may be able to provide a more accurate total energy expenditure estimate during these types of intermittent training activities.

Figure 14:
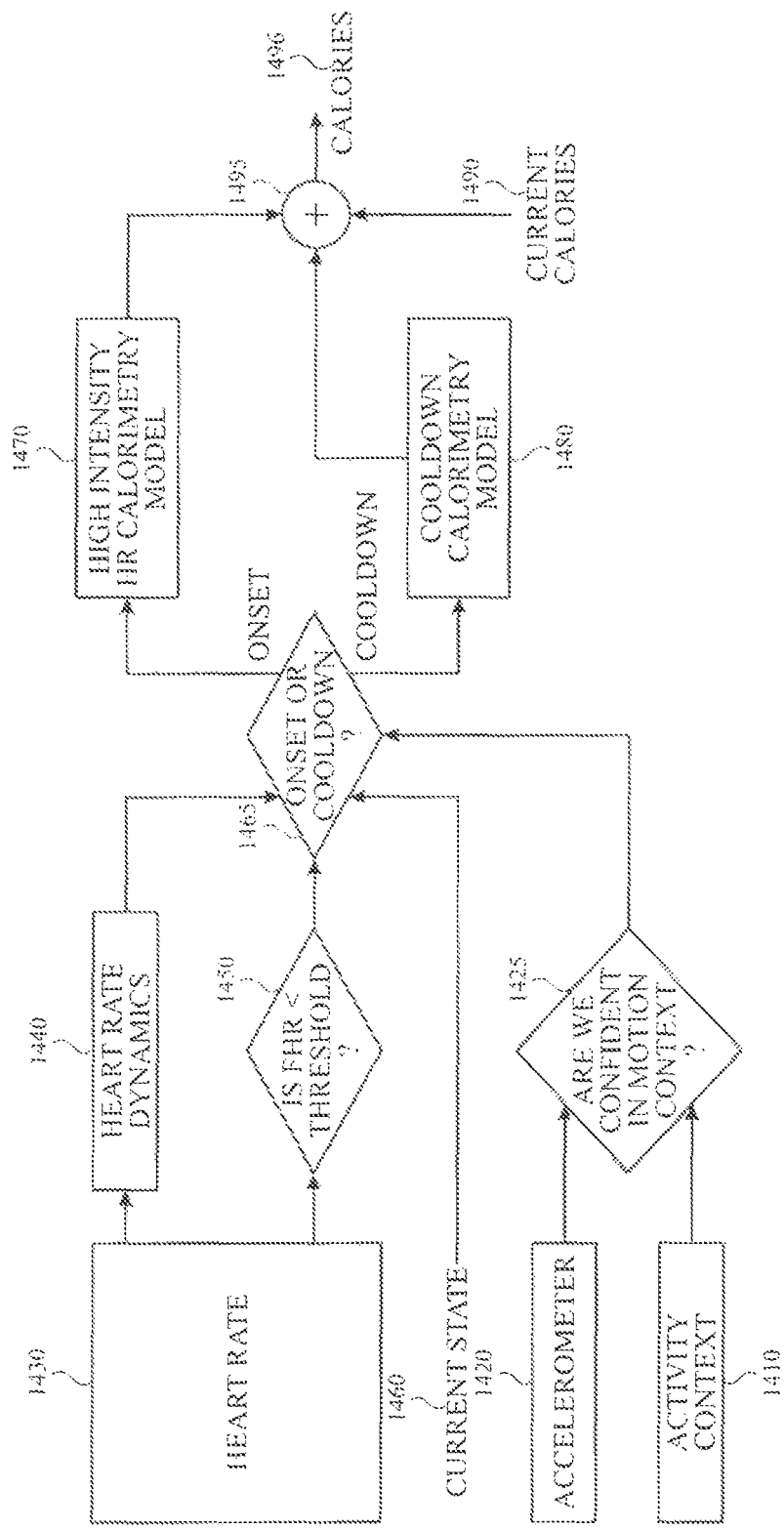
FIG. 14 shows a calorimetry method for intermittent activity in accordance with an embodiment of the present disclosure.

FIG. 14 shows a calorimetry method for intermittent activity in accordance with an embodiment of the present disclosure. At block 1410, an activity context may be determined. For example, in some embodiments, the fitness tracking device 100 may receive an indication from the user that the user is going to begin a session of intermittent activity (e.g., cross-training, interval running, yoga, weight lifting, etc.).

In parallel, at block 1420, motion data from an accelerometer, e.g., motion data form motion sensing module 220, may also be provided to block 1425.

At block 1425, a determination may be made as to whether the fitness tracking device is confident that the activity context is an intermittent activity based on the motion data from block 1420 and an activity context from block 1410. A confidence level may be output to block 1465.

At block 1430, an instantaneous heart rate may be obtained from a heart rate sensor, e.g., heart rate data from heart rate sensing module 210, may be provided to blocks 1440 and 1450.

At block 1440, a heart rate dynamics analysis may be performed. For example, a first (smoothed) derivative and a second (smoothed) derivative of a sequence of heart rate samples may be computed. The derivatives may be analyzed to predict whether the user is experiencing onset or cool-down.

For example, if the first derivative is positive (i.e., heart rate is increasing) and the second derivative is positive (i.e., heart rate is not only increasing; the rate at which heart rate is increasing is also increasing), there may be a relatively high confidence that the user is experience onset.

For another example, if the first derivative is negative (i.e., heart rate is decreasing) and the second derivative is zero (i.e., the rate at which heart rate is decreasing is constant) or the second derivative is negative (i.e., the rate at which heart rate is decreasing is also decreasing), there may be a relatively high confidence that the user is experiencing cool-down.

Additionally, heart rate data from block 1430 may also be used to compute a current normalized heart rate (NHR) or fraction of heart rate reserve (FHR). At block 1450, a determination may be made as to whether FHR exceeds a threshold level of FHR as a clue for onset or cool-down detection. For example, if FHR exceeds the threshold, it may be more likely that the user is experiencing onset of intermitting activity, whereas if FHR is less than the threshold, it may be more likely that the user is experience cool-down.

At block 1460, an indication of "current state" (e.g., the most recent determination of the user being in an onset state or cool-down state) may be fed back into block 1465 so that the calorimetry process may account for onset/cool-down hysteresis.

At block 1465, a determination may be made as to whether the user is currently experiencing onset or cool-down. The determination process at block 1465 may account for clues from a variety of sources, such as activity context and confidence in activity context received from block 1425, heart rate dynamics clues received from block 1440, an indication of whether FHR exceeds a threshold value from block 1450, and feedback about the previously determined current state from block 1460.

The determination of onset or cool-down state at block 1465 may be used to select an appropriate calorimetry model. For example, if it is determined at block 1465 that the user's (new) current state is onset, FHR may be used as a feature input to a heterogeneous, generic, high-intensity calorimetry solution for estimating calories burned during the onset condition at block 1470.

For another example, if it is determined at block 1465 that the user's (new) current state is cool-down, a custom time domain decay equation may be used to model "passive" calorie burn during cool-down at block 1480. In some embodiments, the cool-down calorimetry model at 1480 may use a custom time domain decay equation, which may be parameterized based on the active calorie intensity at the beginning of a cool-down phase, the elapsed duration of the current cool-down phase, and the FHR.

At block 1495, and accumulator may be used to add current calories burned (block 1490) to the accumulated total (block 1496).

In some embodiments, the high-intensity heart rate-based calorimetry model selected for onset conditions may be similar or the same as the heart rate-based calorimetry model selected for "non-intermittent" activities (e.g., running, cycling) and may be computed based at least in part on the user's heart rate or FHR.

In some embodiments, the cool-down calorimetry model may be configured to compute Excess Post-Exercise Oxygen Consumption (EPOC). After an individual finishes exercising, or when an individual is temporarily at rest during an intermittent exercise such as cross-training or weight lifting, the individual may enter a cool-down period during which oxygen consumption (and heart rate) are elevated. For example, if two users are sitting in chair at rest, but the first user has just sit down after running for an hour, the first user will temporarily consume more oxygen (and expend more energy) than the second user who has been sitting for the past hour. EPOC is the "excess" (extra) oxygen consumption that an individual consumes during a cool-down period after exercising.

A calorimetry model that accounts for EPOC may be more accurate because it may be able to distinguish between the two sitting users in the example above, the first of whom was experiencing EPOC during cool-down.

The total EPOC may be attributable to: 1) short-term replenishment of quick-discharge power reserves (e.g., adenosine triphosphate, or ATP), 2) long-term replenishment of run-of-the-mill power reserves (e.g., glycols), 3) anaerobic expenditure-created oxygen deficits, and 4) physiological conditions during cool-down (e.g., higher body core temperature, which may indicate a higher metabolic rate). EPOC may include both a relatively fast decaying component and a relatively slowly decaying component.

Breaking EPOC down into its component parts and modeling each part may allow for more accurate calorimetry, particularly during intermittent exercises when individuals may switch frequently between periods of onset and cool-down.

The fast decaying component may be based on a fixed decay rate based on the user's physical characteristics (e.g., age, body mass index or BMI, and sex) and the user's fitness boundaries (e.g., a PAL score). In some embodiments, the fast decay function may be modeled as:

$$\dot{V}O_2(t)=\dot{V}O_2(0)\cdot 2^{-t/30} \quad \text{(Eq. 5A)}$$

According to Equation 17, the user's oxygen consumption at time t, which may be used to estimate energy expenditure at time t, is based on the user's oxygen consumption at time t=0 when the current cool-down phase began, adjusted by the fast decay factor $2^{-t/30}$.

The slow decaying component may be based on a decay rate on the order of several hours, which depends on fitness level (e.g., aerobic capacity, PAL score, etc.), as well as activity intensity and duration. In some embodiments, the slow decay function may be modeled as:

$$\dot{V}O_2(t)=\dot{V}O_2(0)\cdot 2^{-t/(100-\dot{V}O_2max)} \quad \text{(Eq. 5B)}$$

According to Equation 18, the user's oxygen consumption at time t, which may be used to estimate energy expenditure at time t, is based on the user's oxygen consumption at time t=0 when the current cool-down phase began, adjusted by the slow decay rate that includes $\dot{V}O_2max$ as part of its calculation.

The total EPOC may be attributable to: 1) short-term replenishment of quick-discharge power reserves (e.g., adenosine triphosphate, or ATP), 2) long-term replenishment of run-of-the-mill power reserves (e.g., glycols), 3) anaerobic expenditure-created oxygen deficits, and 4) physiological conditions during cool-down (e.g., higher body core temperature, which may indicate a higher metabolic rate). Taken together, the total EPOC (i.e., volume of oxygen consumed), which may be used to determine calories burned during cool-down, may be modeled as:

$$\dot{V}O_2(t)=(\alpha_1)\dot{V}O_2(0)\cdot 2^{-t/30}+(\alpha_2)\dot{V}O_2(0)\cdot 2^{-t/(100-\dot{V}O_2max)}+(\alpha_2)FHR+\alpha_4 \quad \text{(Eq. 5C)}$$

According to Equation 19, total oxygen consumption at time t during a cool-down phase may be given as the weighted sum of the four main components of EPOC. The parameters $\alpha_1$-$\alpha_4$ may be assigned default values based on a training set. In some embodiments, a different set of parameters based on different corresponding training sets may be used depending on the determined activity context. For example, one set of parameters may be used for a cross-training activity context, and a different set of parameters may be used for an interval running activity context. In some embodiments, the parameters may be calibrated or otherwise adjusted according to an individual's physical characteristics or fitness level.

Calorimetry—Pedometry-Based calorimetry

For low-intensity activities (e.g., walking), a pedometry-based calorimetry process may be more accurate than the heart rate and work rate-based calorimetry processes explained above.

As explained above with reference to FIGS. 5-10, pedometer functionality in the fitness tracking device 100 may be used for determining time spent or distance traversed while engaged in sedentary or modest levels of physical activity. In some embodiments, the fitness tracking device 100 may be configured to estimate energy expenditure for the time spent or distance traversed during moderate levels of activity such as walking.

In some embodiments, pedometer functionality in the fitness tracking device 100 may also be used for determining time spent or distance traversed while engaged in other levels of physical activity, including moderate or intense levels activities. The fitness tracking device 100 may be configured to estimate energy expenditure for the time spent or distance traversed during intense levels of activity such as running. For example, if there is too much noise in a heart signal to use heart rate-based calorimetry, relatively intense activity may still be accounted for by, e.g., pedometry functionality.

Calorimetry—Posture-Based calorimetry

As explained above, a user will also burn calories while sedentary (e.g., sleeping, sitting, standing, or otherwise "at rest"), and calorimetry models vary depending on the type of sedentary activity (e.g., sitting burns fewer calories than standing). Additionally, incidental motion (e.g., fidgeting) while sitting or standing burns more calories than when there is not incidental motion.

In some embodiments, the fitness tracking device 100 may provide more accurate day-long calorimetry by also accounting calories burned during sedentary activities. By performing posture detection (e.g., detecting whether the user is sitting or standing), an appropriate calorimetry model may be selected according to the user's detected posture.

Figure 15:
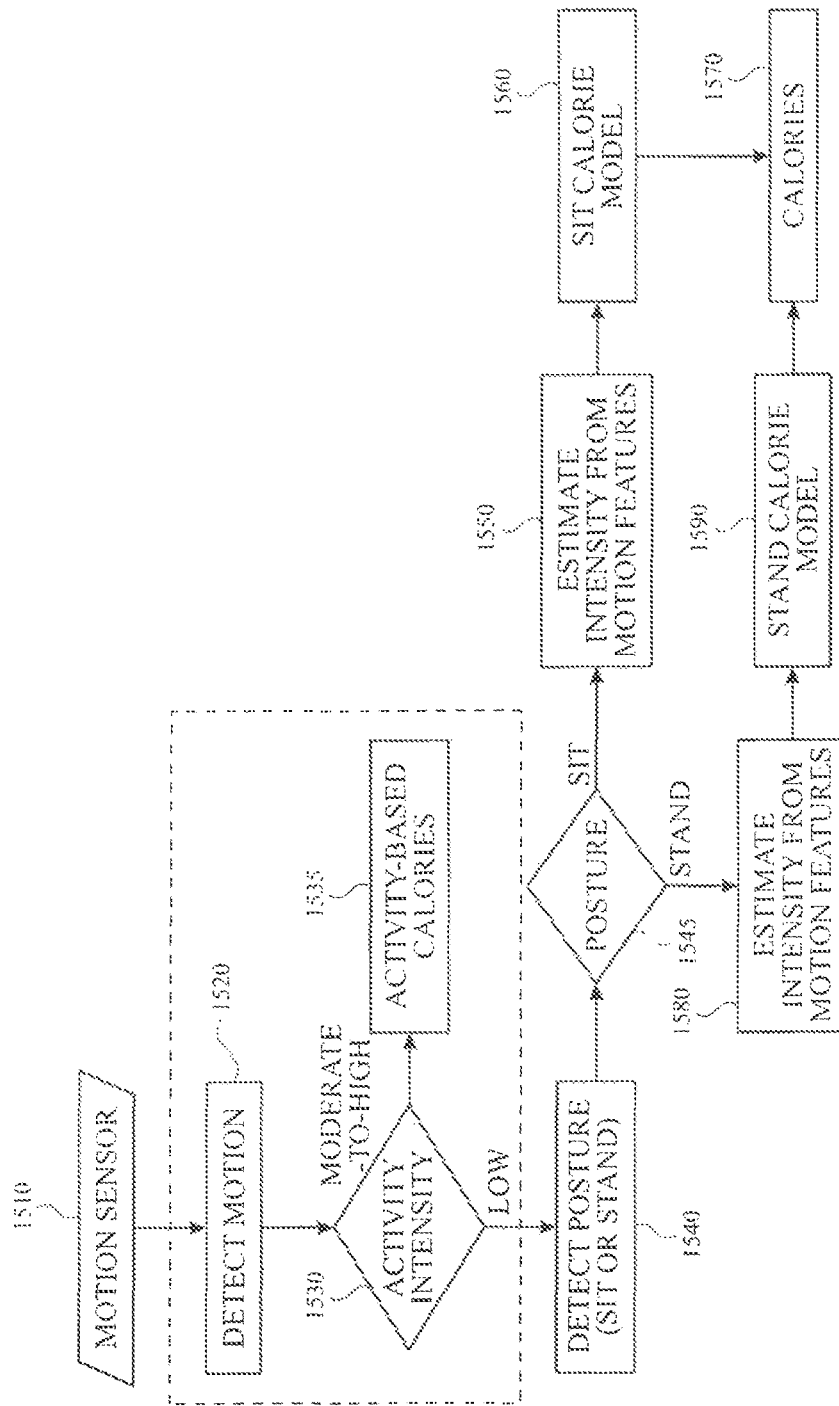
FIG. 15 shows a posture detection method for sedentary calorimetry in accordance with an embodiment of the present disclosure.

FIG. 15 shows a posture detection method for sedentary calorimetry in accordance with an embodiment of the present disclosure. At blocks 1510 and 1520, motion data from a motion sensor (e.g., motion data from motion sensing module 220) may be provided to block 1530.

At block 1530, a determination of activity intensity may be made based on the motion data received from block 1520. If the activity intensity is estimated to be moderate-to-high intensity, the fitness tracking device 100 may use an activity-based calorimetry model at block 1535. However, if it is determined at block 1530 that the activity intensity is low (e.g., sedentary), the method may proceed to block 1540.

At blocks 1540 and 1545, posture (e.g., sitting or standing) may be detected. Posture detection is explained in more detail below with reference to FIGS. 16-19B. If a determination is made at block 1545 that the user is sitting, the method may proceed to block 1550. If a determination is made at block 1545 that the user is standing, the method may proceed to block 1580.

At block 1550 (i.e., user was determined to be sitting), intensity may be estimated based on motion data from blocks 1510 and 1520. For example, the motion data may indicate how much the user is "fidgeting" (e.g., incidental movement, swaying, etc.), so an amount of fidgeting may be detected at block 1550, and the amount of fidgeting may be passed to block 1560. Incidental movement or fidgeting may be relatively low while sitting (e.g., typing, turning a steering wheel, etc.), and incidental movement may be relatively high while standing (e.g., arm movement while washing dishes, folding laundry, etc.).

At block 1560, a calorie model for sitting may be applied to estimate calorie expenditure while sitting and possibly also fidgeting. The calories may be output at block 1570.

At block 1580 (i.e., user was determined to be standing), intensity may be estimated based on motion data from blocks 1510 and 1520. For example, fidgeting (while standing) may be detected at block 1580, and an indication of whether the user is fidgeting while standing may be passed to block 1590. Fidgeting as a generic term may include motion due to performing low-intensity activities while standing. For example, slowly pacing, washing dishes, cooking, walking up stairs, etc. are low-intensity activities that require more energy expenditure than standing still. These activities with additional movement may be detected as relatively intense "fidgeting."

At block 1590, a calorie model for standing may be applied to estimate calorie expenditure while standing and possibly also fidgeting. The calories may be output at block 1570.

Calorie models for sitting and standing may be assigned default values (e.g., 1 MET for sitting and 2 METs for standing, or 1.5 METs for sitting and 2.5 METs for standing). Additional METs may be credited depending on whether the user is fidgeting and the relative intensity of the fidgeting. In some embodiments, the calorie models may be selected to be higher or lower than values reported in the literature for these activities to reduce the amount of generalization error that may occur across different user populations. In some embodiments, at least the initial calorie models may be based on training data. In other embodiments, the calorie models may be calibrated or otherwise adjusted according the user's physical characteristics or fitness level.

Figure 16:
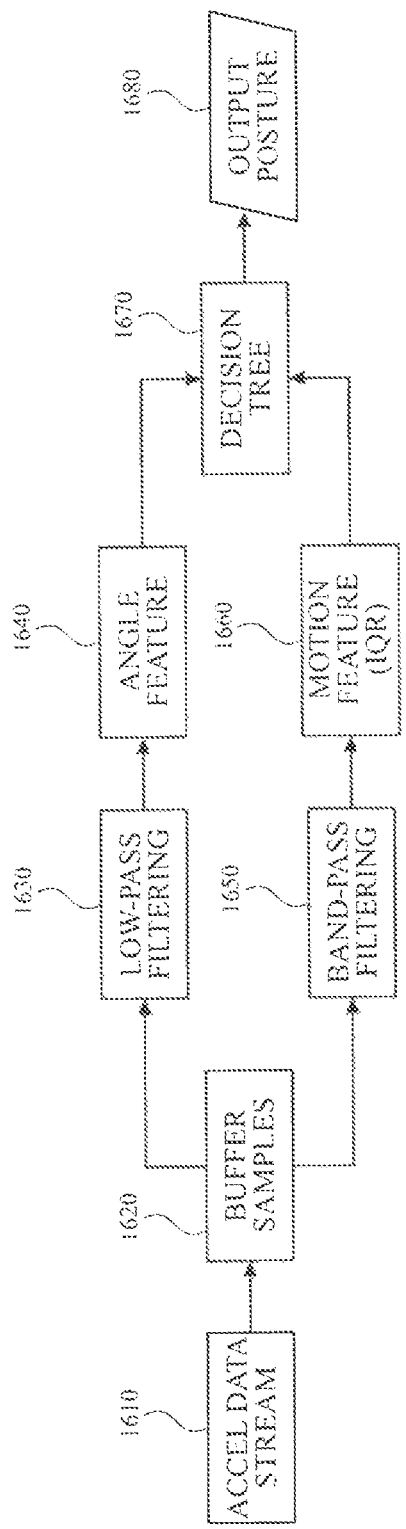
FIG. 16 depicts a posture detection method in accordance with an embodiment of the present disclosure.

FIG. 16 depicts a posture detection method in accordance with an embodiment of the present disclosure. At block 1610, a stream of motion data (e.g., accelerometer data) may be provided to block 1620.

At block 1620, samples of motion data from the stream of motion data may be taken at a suitable resolution (e.g., 200 samples). 200 samples may be taken at a frequency of 100 Hz over a time period of 2 seconds. In other embodiments, other sample rates may be used (e.g., 256 samples or 1,000 samples), or other sample frequencies may be used (e.g., 50 Hz, or 200 Hz). Copies of the samples may be passed to blocks 1630 and 1650. For example, a longer duration epoch of 10 seconds may be taken to collect 1,000 samples. However, longer durations may be less accurate because multiple posture changes could occur within a single epoch (e.g., a longer ten-second epoch). Similarly, shorter epochs may be less accurate because they may not provide a sufficient number of samples to detect posture accurately.

At block 1630, low-pass filtering (LPF) may be performed to subtract out frequencies attributable to fidgeting or other incidental motion. The remaining information (i.e., the portion of motion data that tends to change slowly) may reflect the orientation of the fitness tracking device 100 (e.g., the angle of the fitness tracking device 100 with respect to the horizon, explained in detail below). For example, if a user is standing with arms at the user's side, the user might be fidgeting, but the angle of the fitness tracking device on the user's arm (e.g., approximately $-\pi/2$ radians) may only vary slightly during a short time period (e.g., 2-3 seconds). This angle information may be represented in relatively low frequencies (e.g., less than 0.5 Hz, or less than 1.0 Hz), and this low frequency signature may be passed to block 1640.

At block 1640, the relatively low frequency signature from block 1630 may be used to compute the angle of the fitness tracking device 100 with respect to a horizon plane (e.g., the X-Y plane). The computed angle (e.g., approximately $-\pi/2$ radians) may be passed to block 1670 as one of the inputs to be considered with a decision tree at block 1670.

At block 1650, band-pass filtering may be performed to obtain human motion information contained in a relatively higher frequency band (e.g., over 0.5 Hz, or over 1.0 Hz, and up to 5.0 Hz, or 4.0 Hz), such as fidgeting or other incidental motion. This band's frequency signature may be passed to block 1660. The band-pass filter may be configured with a frequency band (e.g., 1.0-5.0 Hz) tuned to capture human motion likely to occur when the user is sedentary (e.g., fidgeting or incidental motion). In some embodiments, if it may be determined that more rapid (e.g., higher frequency) human motion is likely to occur while sedentary, the frequency band of the band-pass filter may be calibrated or otherwise adjusted accordingly.

At block 1660, the band's frequency signature from block 1650 may be used to predict posture based on the motion data received from block 1650. In some embodiments, the prediction may be based on the assumption that the range of motion (e.g., range of wrist motion, such as when a user's arms are swaying) while standing is likely to be greater than the range of motion (e.g., wrist motion) while the user is sitting. The range of motion may be estimated based on the motion data received from block 1650, which may have been filtered using a band-pass filter to include motion that may likely be attributable to human motion (e.g., fidgeting).

In some embodiments, the relative range of motion during a given time period (or "epoch") may be represented as a range of amplitudes of accelerometer values. For example, the interquartile range (IQR) between the 75th percentile and 25th percentile accelerometer amplitudes over a number of samples (e.g., 250 samples) during the time period may be considered for the range of motion. For example, it some embodiments, a typical separation in ranges of motions for IQR while sitting as opposed to IQR while standing may be determined to be greater than or equal to approximately 0.1 to 0.2 meters.

Furthermore, it may be determined that a particular axis or combination of axes of a three-axis accelerometer within the fitness tracking device 100 provides the most reliable IQR to distinguish between motion likely occurring while standing as opposed to motion likely occurring while sitting. In some embodiments, for example, the x-axis of the accelerometer may be determined to provide the most reliable IQR. In other embodiments, a default axis or weighted combination of axes may be selected, and the selected axis or axes may be calibrated or otherwise adjusted based on individual use. For example, the typical incidental motion for a user relative to the typical position and orientation of the fitness tracking device 100 on the user's wrist or other part of the body may affect which axis or combination of axes may provide the most useful range of motion data for the IQR motion feature. This IQR motion feature may be passed to block 1670 as a second input to be considered with the decision tree at block 1670.

At block 1670, the computed angle feature and the computed IQR motion feature may be considered in the decision tree (e.g., a sequence of "if-else" conditional branches using a model with thresholds for angle and motion values). Once a posture decision has been made (e.g., the user is sitting or the user is standing), the posture may be output at block 1680. For example:

---

If (Angle < −0.5 radians and IQR > 0.1)
   Return "Standing"
Else If (−0.5 radians < Angle < 0 radians and IQR > 0.2)
   Return "Standing"
Else If . . .

In the example decision tree above, the first condition (Angle<−0.5 radians and IQR>0.1) may represent typical parameters when a user's hands are well below a horizon, though not necessarily vertically at the user's sides. Because the angle may be sufficiently unambiguous, it may be less important to observe a relatively large IQR to estimate that the user is probably standing. In the second condition (−0.5 radians<Angle<0 radians and IQR>0.2), the angle may be considered more shallow, and more ambiguous (e.g., the user's arms are crossed). In this situation, a relatively ambiguous angle may make it relatively more important to observe a relatively large IQR to estimate that the user is probably standing.

Other conditions, or additional portions of the conditions listed above, may be included in other embodiments. For example, another condition (not shown above) may indicate that if the angle is a positive value, it may be predicted that the user is likely sitting. Alternatively, some positive angles may be considered ambiguous. Another feature for resolving ambiguous angle and IQR features may include a pedometry feature. For example, if a pedometer function of the fitness tracking device 100 determines that the user may be walking (e.g., pacing), the fitness tracking device 100 may conclude that the user had been standing.

In some embodiments, another feature to consider may be the frequency or rapidity of incidental movement (as opposed to the IQR feature described above, which indicates the amplitude or range of incidental movement). Frequency of movement may be determined by observing the number of zero crossings (or variations around the mean) of a value of one or more axes of an accelerometer.

In some embodiments, other features in addition to, or instead of, angle and IQR motion may be considered to detect posture, such as differences between X, Y, and Z accelerometer channels; mean values, vector magnitude, activity counts (e.g., how many times a signal crosses a sit/stand threshold in the epoch window), spectral power, etc. may be considered when detecting the user's posture. For example, in some embodiments, it may be determined that angle and IQR may be less effective than other features for detecting whether a user is sitting or standing with arms crossed. Specifically, standing with arms crossed may restrict motion (e.g., wrist motion) relatively more than when standing without arms crossed. Thus, the IQR feature may be relatively low if a user is standing with arms crossed.

For this case of crossed arms, an activity count may be more likely to predict whether a user is sitting or standing. In some embodiments, the counted activity may be zero crossings over the angle threshold (e.g., angle crossings over the horizon). For example, it may be determined that the angle feature is more likely to cross a threshold angle more frequently when the user is standing as opposed to when the user is sitting, in which case a higher activity count (measured by threshold angle crossings) may be a more accurate predictor of posture in this situation.

In some embodiments, other classifiers in addition to, or instead of, the decision tree may be used to detect posture based on the one or more input features (e.g., the angle and IQR motion features). For example, random forests, a separate sit detector, a separate stand detector, support vector machines, etc., may be used to classify or otherwise detect the user's posture.

In some embodiments, a feedback or hysteresis mechanism may be used to smooth out possible noise in the detection output. For example, the method may track the previous four epoch states (or more or fewer epoch states) and consider a confidence level or other indicator of which of the current or prior epoch states may be determined to be the dominant or most confident indicator of posture.

In some embodiments, the classifier (e.g., the decision tree used at block 1670) may be biased toward detecting a sitting posture more frequently. For example, ambiguous states may be more likely to be resolved as a sitting posture instead of a standing posture. In this situation, there may be fewer false positives for a standing posture, which makes it less likely that users who are sitting will not receive additional credit for extra energy expenditure for standing while they were sitting. In other embodiments, the decision tree may be biased to break-ties in favor of standing, which may make it less likely that a user who is standing may be docked credit for a false positive sit detection.

Figures 17, 18:
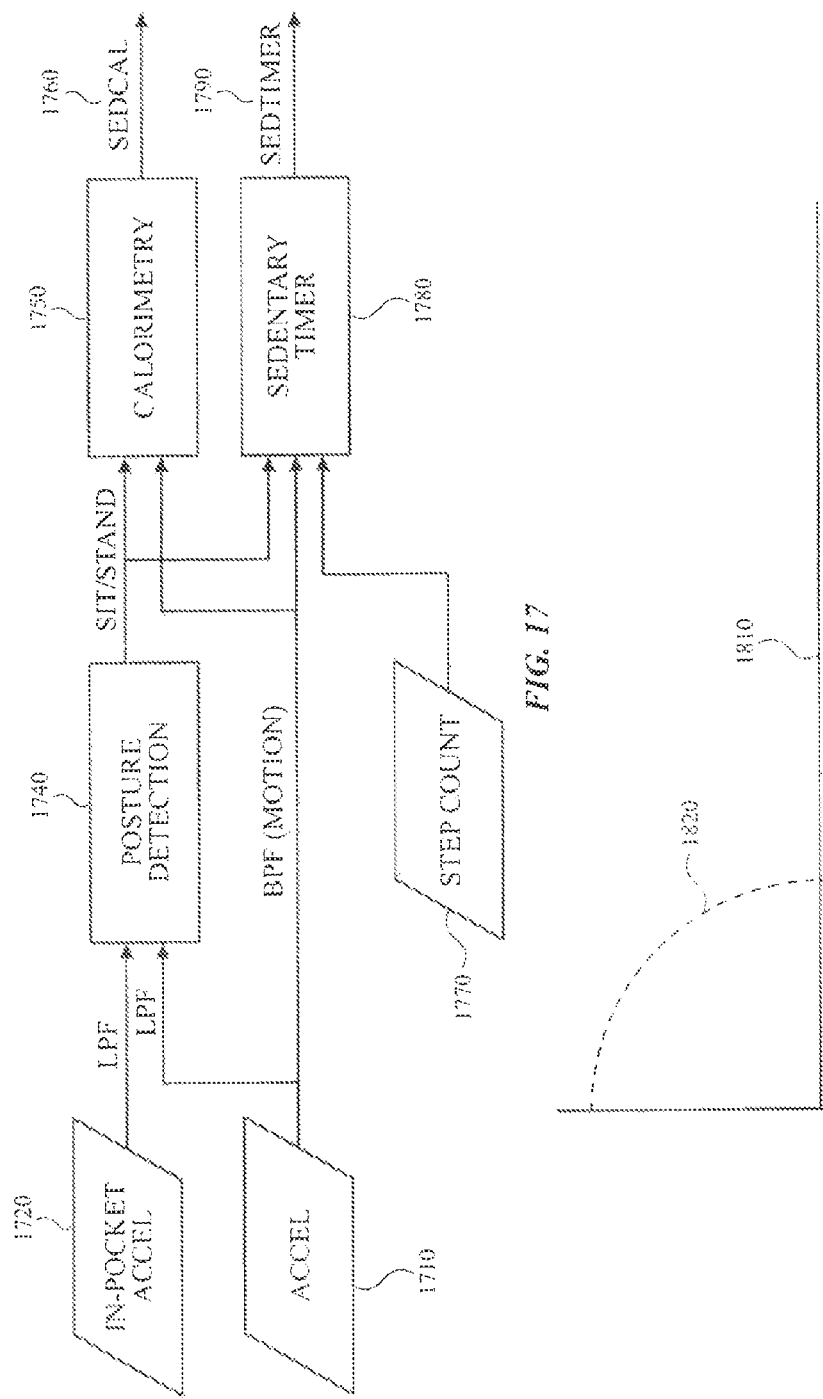
FIG. 17 shows a posture detection method for sedentary activity in accordance with an embodiment of the present disclosure.
FIG. 18 illustrates a posture detection technique in accordance with an embodiment of the present disclosure.

FIG. 17 shows a posture detection method for sedentary activity in accordance with an embodiment of the present disclosure. In some embodiments, the posture detection techniques may account for additional data from the companion device 300. As shown in FIG. 17, accelerometer data may be received at block 1710 (from, e.g., motion sensing module 220 of the fitness tracking device 100), and accelerometer data may be received at block 1720 (from, e.g., the companion device 300, when it may be determined that the companion device is in the user's pocket). Accelerometer data from both the fitness tracking device 100 (e.g., from block 1710) and the companion device 300 (e.g., from block 1720) may be passed to block 1740.

At block 1740, the user's posture may be detected. In some embodiments, the posture detection method may be similar to the method described with reference to FIG. 16. The filters and the classifier (e.g., decision tree) may also take into account an angle feature and an IQR feature or other features from the companion device 300. The decision tree may include different threshold values, weightings, and confidence levels for the companion device 300. For example, if the companion device is detected to be in the user's pocket and oriented vertically, there is a strong indication that the user is standing, even if the user's arms are crossed into a relatively ambiguous sit/stand position with respect to the fitness tracking device 100. As another example, the fitness track device 100, which may be worn on the wrist, may, at least for some activities, receive more indications of fidgeting or other incidental movement than a companion device stored in a pocket near the user's hip. The detected posture (e.g., sit or stand) may be passed to blocks 1750 and 1780.

At block 1750, a calorimetry process may compute energy expended according to a calorimetry model based on the posture detected at block 1740. The calorimetry process may also account for calories burned due to incidental motion (e.g., fidgeting), which may be detected using the IQR motion feature passed from block 1710 through a band-pass filter. The sedentary calorie count ("SedCal") may be outputted at block 1760.

FIG. 17 also includes a timer feature for tracking how much time is spent in sedentary postures, such as with limited incidental motion below a predetermined threshold. In some embodiments, a step count may be determined at block 1770 (e.g., using pedometer functionality of the fitness tracking device 100). The step count may be passed to block 1780.

In some embodiments, at block 1780, a timer may track whether the user is sedentary, and for how long. It may account for detected posture received from block 1740, IQR motion feature received from block 1710, step count received from block 1770, etc. The amount of sedentary time ("SedTimer") may be output at block 1790. In some embodiments, if the sedentary timer detects that a user has been sitting or otherwise sedentary for a prolonged period of time, the fitness tracking device 100 may be configured to alert the user to encourage the user to stand up or otherwise move around.

FIG. 18 illustrates a posture detection technique in accordance with an embodiment of the present disclosure. As shown in FIG. 18, horizontal line (1810) represents the horizon 1810 (e.g., the X-Y horizon plane). A first arc 1820 represents angles above the horizon 1810. A second arc 1730 represents angles below the horizon 1810. In the example of FIG. 18, a threshold angle may be set at 0 radians (i.e., in-line with the horizon 1810). If the detected angle feature is an angle within the first arc 1820, the classifier (e.g., decision tree) may consider it a strong clue that the user has a first posture (e.g., sitting). Similarly, if the detected angle feature is an angle within the second arc 1730, the classifier may determine that the user has a second posture (e.g., standing).

In some embodiments, the orientation of the fitness tracking device relative to the horizon plane (e.g., horizon 1810) may be determined based on motion data received from a three-axis accelerometer, a three-axis gyroscope, or a combination of a three-axis accelerometer and a three-axis gyroscope, such as the motion sensors that may be included in motion sensing module 220 of the fitness tracking device 100.

In other embodiments, a different threshold angle may be selected to indicate which range of angles are more likely to be assumed while in a sitting posture, and which range of angles are more likely to be assumed while in a standing posture. In some embodiments, the ranges may overlap, and the overlapping regions are angles for which the posture may be ambiguous.

FIGS. 19A-B illustrate posture detection techniques in accordance with embodiments of the present disclosure. As shown in FIG. 19A, a first user 1910 is standing with arms at the user's side. The first user 1910 is wearing the fitness tracking device 100 on the user's wrist, and it is oriented at an angle 1915 that is below the horizon 1810. In this example, a posture detection algorithm may evaluate the angle 1915 and determine correctly that the first user 1910 is standing.

As shown in FIG. 19B, a second user 1920 is sitting with arms extended out, typing on a keyboard while sitting at a desk. The second user 1920 is also wearing the fitness tracking device 100 on the user's wrist, and it is oriented at an angle 1925 that is approximately at the horizon 1810. In this example, a posture detection algorithm may consider this angle to be ambiguous. For example, the angle may be insufficient to distinguish between a user sitting and typing or standing with arms crossed at an angle roughly level with the horizon.

In this case, it may be possible to resolve the ambiguity based on IQR motion. If the user is sitting, as the second user 1920 is sitting, it may be more likely that IQR motion will be relatively low as compared to the IQR motion of a user standing with arms in as similar orientation.

Additionally, the second user 1920 is depicted as holding the companion device 300 in a pants pocket. In some embodiments, it may be detected that the companion device 300 is in the pocket and oriented horizontally, in-line with the horizon 1810. This orientation of the companion device 300 may be a strong indicator that the second user 1920 is in a sitting posture.

Calorimetry—Additional Optimizations for Resource-Constrained Devices

The fitness tracking device 100 may be a small device with limited space for memory and a battery, and it may be designed to be worn all day while running on battery power. Consequently, some embodiments may include optimizations to perform functions within relatively limited resources as compared to the companion device 300 or another computing device. For example, the fitness tracking device 100 may use a low-power motion coprocessor to monitor motion data with less power usage than if the primary microprocessor were continuously monitoring the motion data. As another example, the fitness tracking device 100 may reduce the frequency at which it monitors heart rate data to conserve power until the fitness tracking device 100 detects or otherwise determines that the user is engaged in an activity for which the calorimetry process would benefit from more frequent heart rate monitoring.

To illustrate the benefits of the local model for at least certain circumstances, FIG. 20 shows a speed-based calorimetry method in accordance with an embodiment of the present disclosure.

In some embodiments, the fitness tracking device 100 may be configured to predict energy expenditure using a comparably accurate but less resource-intensive calorimetry process dubbed the "local model." At block 2010, accelerometer or other motion data 2015 may be passed to blocks 2020 and 2030.

At block 2020, speed may be estimated based on the motion data received from block 2010. In some embodiments, the accuracy of the speed estimate 2025 may be improved with GPS location data (e.g., GPS location data received from the companion device 300). The speed estimate may be provided to block 2040

At block 2030, other features may be determined from the motion data or other inputs. These other features may also be provided to block 2040.

At block 2040, a calorimetry model may be used to estimate energy expenditure based on estimated speed 2025 from block 2020 and other input features from block 2030. The calorimetry model may be selected to balance accuracy with complexity (whereby complexity may place increased strains on device resources, such as processing power, memory, battery life, etc.)

For example, the American College of Sports Medicine (ACSM) has a (nonlinear) model for energy expenditure while walking $$\dot{V}O_2 = 0.1(\text{speed}) + 1.8(\text{speed})(\text{fractional grade}) + 3.5 \quad \text{(Eq. 6A)}$$

Equation 6A is a nonlinear model relying on speed and, optionally, grade, as the only inputs. The parameterization is offered as a one-size-fits-all approach. This calorimetry model has minimal complexity, but it may also have low accuracy, particularly for users who are "average" for whom the given parameters may not be a good fit.

At the other end of the spectrum may be highly complex (and/or nonlinear) techniques such as context-aware machine learning models (e.g., neural networks, regression trees, random forests, etc.). A random forest, for example, may be a highly accurate but also can be a highly complex nonlinear model, which may require more time and computing resources (including memory and batter power).

The local model may offer high accuracy that is comparable to a random forest, but the complexity (and therefore the resource requirements) may be substantially lower than those of the random forest.

Figure 21:
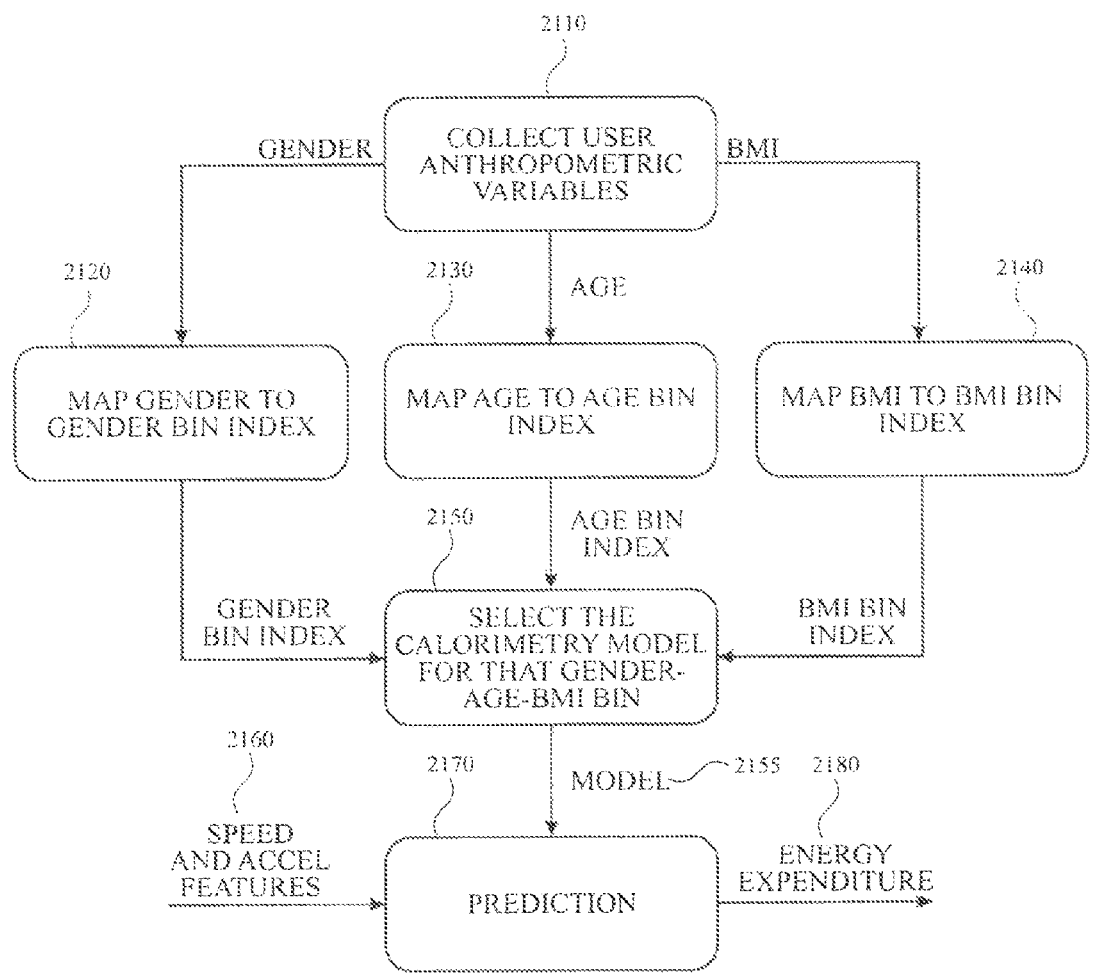
FIG. 21 shows a calorimetry technique using local models in accordance with an embodiment of the present disclosure.

FIG. 21 shows a local model-based calorimetry method in accordance with an embodiment of the present disclosure. Unlike the ACSM's one-size-fits-all model, the local model may still account for differences among users based on age, sex, body mass index (BMI), etc. Instead of building a customized model for every permutation of age, sex, and BMI, each variable may be grouped into a suitable number of bins (or groups). For example, age may be split into bins such as 20-29, 30-39, 40-49, 50-59, etc., and BMI can be split into bins such as 16-19.9, 20-23.9, 24-27.9, 28-31.9, etc. In other embodiments, fewer bins or more bins may be used for age or BMI, and different ranges may be selected.

As shown in FIG. 21, physical characteristics ("anthropomorphic variables") may be collected. These characteristics may include sex (e.g., male or female, sometimes referred to as "gender"), age (e.g., 0-120), and BMI (e.g., 16-32). In some embodiments, the fitness tracking device 100 may receive the user's height and weight to determine the user's BMI. In other embodiments, more or fewer characteristics or variables may be taken into account.

At block 2120, sex ("gender") may be mapped to a "sex bin index" (or "gender bin index") (e.g., female=index 0, male=index 1).

At block 2130, age may be mapped to an "age bin index." For example, using the age bins described above, if the user's age is given as 42, the user's age falls into the "40-49" bin. This bin may be designated as age bin index number 2.

At block 2140, BMI may be mapped to a "BMI bin index." For example, using the BMI bins described above, if the user's BMI is given as 21.2, the user's BMI falls into the "20-23.9" bin. This bin may be designated as bin index number 1.

In other embodiments, other variables may be similarly mapped as the sex, age, or BMI mappings described above.

At block 2150, a calorimetry model may be selected based on the sex bin index number received from block 2120, the age bin index number received from block 2130, and the BMI bin index number received from block 2140. For example, in some embodiments, a calorimetry model trained, calibrated, or otherwise adjusted for a particular permutation of sex, a sub-range (bin) of ages, and a sub-range (bin) of BMI values. Because each variable may be indexed to a relatively small number of bins, only a relatively small number of calorimetry models need to be stored or generated. In some embodiments, the sub-ranges for each bin and the size of each bin may be configured to provide an appropriate balance between accuracy and complexity.

In one example, the ACSM model may be generalized:

$$\dot{V}O_2 = \alpha_1(\text{speed}) + \alpha_2(\text{speed})(\text{fractional grade}) + \alpha_3 \quad \text{(Eq. 6B)}$$

In the general form, the (nonlinear) ACSM model has three coefficients $\alpha_1$-$\alpha_3$. The local model technique may store the three coefficients suitable for each permutation of bins. Thus, in an example for which there are 2 sex bins, 4 age bins, and 4 BMI bins, this configuration may store coefficients for 2×4×4=32 permutations of bins.

The memory required to store 32 triplets of coefficients may be modest compared to a more complex technique and may not be meaningfully larger than storing only single one-size-fits-all model. For example, for a conventional decision tree, the computational complexity may be proportional to the depth of the tree d, which may be generally between 10 and 20. Because the storage required may be proportional to $2^d$, which is on the order of one thousand to one million sets of coefficients. For another example, a random forest may typically require one hundred times more storage than a decision tree. In some embodiments, in which a linear model is used, only 32 pairs or doublets of coefficients may need to be stored. For higher-order nonlinear models, additional parameters may need to be stored for each permutation.

Also, the model selection technique of sorting variables into predetermined bins, and using the bin index numbers to look up a set of coefficients in a relatively small lookup table may require much less battery power and processing power than a more complex technique such as a random forest. Furthermore, once a model is selected, it may require no more battery power, processing power, or memory than a one-size-fits-all model.

At block 2170, an energy expenditure prediction process may use the model 2155 received from block 2150 to estimate energy expenditure given the speed and other inputs provided from block 2160.

At block 2180, the estimated energy expenditure may be outputted.

CONCLUSION

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of at least one particular implementation in at least one particular environment for at least one particular purpose, those of ordinary skill in the art will recognize that its usefulness is not limited thereto and that the present disclosure may be beneficially implemented in any number of environments for any number of purposes.

The invention claimed is:

1. A method of determining posture, the method comprising:
    collecting, a first motion sensor of a fitness tracking device being wearable on a wrist of a user, motion data of the user over a period of time, wherein the motion data comprises a first plurality motion measurements, wherein the fitness tracking device further comprises a processor, the processor communicatively coupled to the first motion sensor, the processor further coupled to a non-transitory readable storage medium, wherein the processor is configured to read instructions stored on the medium;
    receiving, by the processor of the fitness tracking device, the motion data;
    determining, by the processor of the fitness tracking device, using the motion data an angle of the fitness tracking device relative to a plane during the period of time;
    calculating, by the processor of the fitness tracking device, using the motion data, a range of linear motion of the fitness tracking device through space during the period of time;
    comparing, by the processor of the fitness tracking device, the angle of the fitness tracking device to a threshold angle and comparing the range of linear motion of the fitness tracking device to a threshold range of linear motion, wherein the threshold range of linear motion is an interquartile range of linear motion of a first axis of an accelerometer of the fitness tracking device;

determining, by the processor of the fitness tracking device, that the user is standing, wherein determining that the user is standing comprises:
  determining, by the processor of the fitness tracking device, that the range of linear motion of the fitness tracking device is greater than the threshold range, and
  correlating, by the processor of the fitness tracking device, the range of linear motion of the fitness tracking device to an amount of back-and-forth swaying of an arm of the user during the time period; and
outputting, by the processor of the fitness tracking device, an indication that the user is standing.

2. The method of claim 1, wherein the threshold angle is approximately 0 radians relative to the plane, wherein the plane is a horizontal plane, and wherein determining, by the processor of the fitness tracking device, that the user is standing further comprises:
  determining, by the processor of the fitness tracking device, that the angle is less than the threshold angle; and
  correlating, by the processor of the fitness tracking device, the angle of the fitness tracking device to an orientation of an arm of the user below the horizontal plane.

3. The method of claim 1, wherein determining, by the processor of the fitness tracking device, that the user is standing further comprises:
  analyzing the motion data, by the processor of the fitness tracking device, to estimate a frequency of changing direction of linear motion of the fitness tracking device during the period of time; and
  comparing, by the processor of the fitness tracking device, the frequency of changing direction of linear motion to a threshold frequency of changing direction of linear motion.

4. The method of claim 1, wherein determining, by the processor of the fitness tracking device, that the user is standing further comprises:
  determining, by the processor of the fitness tracking device, that a companion device is inside a pocket of the user;
  receiving, by the fitness tracking device, orientation data of the companion device from a second motion sensor of the companion device via a wireless communication protocol; and analyzing, by the processor of the fitness tracking device, the orientation data of the companion device inside the pocket of the user.

5. The method of claim 1, further comprising:
  determining, by the processor of the fitness tracking device, a first rate of energy expenditure of the user based on the indication that the user is standing; and
  determining, by the fitness tracking device, a second rate of energy expenditure of the user associated with the user sitting,
  wherein the first rate of energy expenditure for standing is higher than the second rate of energy expenditure for sitting.

6. The method of claim 1, further comprising resetting a sedentary timer of the fitness tracking device to zero seconds after determining that the user is standing.

7. The method of claim 1, further comprising displaying, by a display of the fitness tracking device, the indication that the user is standing.

8. The apparatus of claim 1, wherein the processor is further configured to output the indication that the user is standing to a display of the fitness tracking device.

9. An apparatus for determining posture, the apparatus comprising:
  a fitness tracking device being wearable on a wrist of a user, the fitness tracking device including a motion sensor; and
  a processor communicatively coupled to the motion sensor, wherein the processor is configured to:
    receive motion data of a user from the motion sensor over a period of time, wherein the motion data comprises a first plurality motion measurements from the motion sensor of the fitness tracking device;
    determine, using the motion data, an angle of the fitness tracking device relative to a plane during the period of time;
    calculate, using the motion data, a range of linear motion of the fitness tracking device through space during the period of time; and
    compare the angle of the fitness tracking device to a threshold angle and compare the range of linear motion of the fitness tracking device to a threshold range of linear motion, wherein the threshold range of linear motion is an interquartile range of linear motion of a first axis of an accelerometer of the fitness tracking device;
    determine that the user is standing, wherein to determine that the user is standing, the processor is further configured to:
      determine that the range of linear motion of the fitness tracking device is greater than the threshold range, and
      correlate the range of linear motion of the fitness tracking device to an amount of back-and-forth swaying of an arm of the user during the time period; and
    output an indication that the user is standing.

10. The fitness tracking device apparatus of claim 9, wherein the threshold angle is approximately 0 radians relative to the plane, wherein the plane is a horizontal plane, and wherein to determine that the user is standing, the processor is further configured to:
  determine that the angle is less than the threshold angle; and
  correlate the angle of the fitness tracking device to an orientation of an arm of the user below the horizontal plane.

11. The apparatus of claim 9, wherein to determine that the user is standing, the processor is further configured to:
  analyze the motion data to estimate a frequency of changing direction of linear motion of the fitness tracking device during the period of time; and
  compare the frequency of changing direction of linear motion to a threshold frequency of changing direction of linear motion.

12. The apparatus of claim 9, wherein to determine that the user is standing, the processor is further configured to:
  determine that a companion device is inside a pocket of the user;
  receive orientation data of the companion device from a second motion sensor of the companion device via a wireless communication protocol; and
  analyze the orientation data of the companion device inside the pocket of the user.

13. The apparatus of claim 9, wherein to determine that the user is standing, the processor is further configured to:
  determine a first rate of energy expenditure of the user based on the indication that the user is standing; and determine a second rate of energy expenditure of the user associated with the user sitting, wherein the first rate of energy expenditure for standing is higher than the second rate of energy expenditure for sitting.

14. The apparatus of claim 9, further comprising:

a sedentary timer, wherein the processor is configured to reset the sedentary timer to zero seconds after determining that the user is standing.

15. An article of manufacture comprising:

a non-transitory processor readable storage medium; and instructions stored on the medium;

wherein the instructions are configured to be readable from the medium by a processor of a fitness tracking device being wearable on a wrist of a user, wherein the fitness tracking device comprises a motion sensor, the instructions thereby causing the processor to:

receive motion data of a user from the motion sensor over a period of time, wherein the motion data comprises a first plurality motion measurements from the motion sensor of the fitness tracking device;

determine, using the motion data, an angle of the fitness tracking device relative to a plane during the period of time;

calculate, using the motion data, a range of linear motion of the fitness tracking device through space during the period of time;

compare the angle of the fitness tracking device to a threshold angle and compare the range of linear motion of the fitness tracking device to a threshold range of linear motion, wherein the threshold range of linear motion is an interquartile range of linear motion of a first axis of an accelerometer of the fitness tracking device;

determine that the user is standing, wherein to determine that the user is standing, the processor is further configured to:

determine that the range of linear motion of the fitness tracking device is greater than the threshold range, and correlate the range of linear motion of the fitness tracking device to an amount of back-and-forth swaying of an arm of the user during the time period; and output an indication that the user is standing.

16. The article of manufacture of claim 15, wherein the threshold angle is approximately 0 radians relative to the plane, wherein the plane is a horizontal plane, and wherein to determine that the user is standing, the processor is further caused to:

determine that the angle is less than the threshold angle; and correlate the angle of the fitness tracking device to an orientation of an arm of the user below the horizontal plane.

17. The article of manufacture of claim 15, wherein to determine that the user is standing, the processor is further configured to:

analyze the motion data to estimate a frequency of changing direction of linear motion of the fitness tracking device during the period of time; and compare the frequency of changing direction of linear motion to a threshold frequency of changing direction of linear motion.

18. The article of manufacture of claim 15, wherein to determine that the user is standing, the processor is further configured to:

determine that a companion device is inside a pocket of the user;

receive orientation data of the companion device from a second motion sensor of the companion device via a wireless communication protocol; and analyze the orientation data of the companion device inside the pocket of the user.

19. The article of manufacture of claim 15, wherein to determine that the user is standing, the processor is further configured to:

determine a first rate of energy expenditure of the user based on the indication that the user is standing; and determine a second rate of energy expenditure of the user associated with the user sitting, wherein the first rate of energy expenditure for standing is higher than the second rate of energy expenditure for sitting.

20. The article of manufacture of claim 15, wherein the processor is further configured output the indication that the user is standing to a display of the fitness tracking device.

* * * * *